United States Patent
Yu et al.

(10) Patent No.: US 11,583,577 B2
(45) Date of Patent: Feb. 21, 2023

(54) CANCER IMMUNOTHERAPY BY IMMUNE ACTIVATION OR IMMUNE MODULATION VIA GLOBO SERIES ANTIGENS

(71) Applicant: OBI PHARMA, INC., Taipei (TW)

(72) Inventors: Cheng-Der Tony Yu, Taipei (TW); Youe-Kong Shue, Taipei (TW); Chen-Hsin Liang, Taipei (TW); Peiwen Yu, Taipei (TW); Chwen-Cheng Chen, Taipei (TW)

(73) Assignee: OBI PHARMA, INC., Taipei (TW)

( * ) Notice: Subject to any disclaimer, the term of this patent is extended or adjusted under 35 U.S.C. 154(b) by 0 days.

(21) Appl. No.: 15/495,470

(22) Filed: Apr. 24, 2017

(65) Prior Publication Data

US 2017/0304419 A1    Oct. 26, 2017

Related U.S. Application Data

(60) Provisional application No. 62/381,875, filed on Aug. 31, 2016, provisional application No. 62/345,755, filed on Jun. 4, 2016, provisional application No. 62/343,530, filed on May 31, 2016, provisional application No. 62/326,623, filed on Apr. 22, 2016.

(51) Int. Cl.
| | |
|---|---|
| *A61K 38/00* | (2006.01) |
| *A61K 39/00* | (2006.01) |
| *A61P 35/00* | (2006.01) |
| *G01N 33/574* | (2006.01) |
| *A61K 45/06* | (2006.01) |

(52) U.S. Cl.
CPC .......... *A61K 39/001173* (2018.08); *A61K 39/00118* (2018.08); *A61P 35/00* (2018.01); *G01N 33/57407* (2013.01); *G01N 33/57415* (2013.01); *G01N 33/57492* (2013.01); *A61K 45/06* (2013.01); *A61K 2039/545* (2013.01); *A61K 2039/55577* (2013.01); *A61K 2039/575* (2013.01); *A61K 2039/6081* (2013.01); *G01N 2400/38* (2013.01); *G01N 2800/52* (2013.01)

(58) Field of Classification Search
CPC ...... A61K 39/001173; A61K 39/00118; A61K 39/0011; A61K 2039/55577; A61K 45/06; A61P 35/00; G01N 33/57407; G01N 33/57415; G01N 33/57492; G01N 2800/52
See application file for complete search history.

(56) References Cited

U.S. PATENT DOCUMENTS

| | | |
|---|---|---|
| 3,773,919 A | 11/1973 | Boswell et al. |
| 4,203,975 A | 5/1980 | Greven |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |

(Continued)

FOREIGN PATENT DOCUMENTS

| | | |
|---|---|---|
| CN | 1871025 A | 11/2006 |
| CN | 103108654 A | 5/2013 |

(Continued)

OTHER PUBLICATIONS

O'Cearbhaill et al, Journal of Clinical Oncology, 31(15), Suppl 1, Abstract 5550, 2013.*
Huang et al, PNAS, 109:17561-17566, 2012.*
Danishefsky et al, Acc Chem Res, 48:643-652, 2015.*
Gilewski et al, PNAS, 3270-3275, 2001.*
Clinical Trial NCT01516307 posted Jan. 24, 2012.*

(Continued)

*Primary Examiner* — Mark Halvorson
(74) *Attorney, Agent, or Firm* — Proysla Group, PC

(57) ABSTRACT

The disclosure provides a method of immunotherapy for a cancer patient, comprises administering vaccines against Globo series antigens (i.e., Globo H, Stage-specific embryonic antigen 3 "SSEA3" and Stage-specific embryonic antigen 4 "SSEA4"). Specifically, the method comprises administering Globo H-KLH (OBI-822) in patients with Metastatic Breast Cancer. The disclosure also provides a method of comprises selecting a cancer patient who is suitable as treatment candidate for immunotherapy. In addition, the disclosure provides therapeutic agents, including monoclonal antibodies (mAbs) that bind specifically to Globo series antigens and related biomarkers useful in focusing such therapeutic and diagnostic regimens.

31 Claims, 14 Drawing Sheets
(12 of 14 Drawing Sheet(s) Filed in Color)

(56) References Cited

U.S. PATENT DOCUMENTS

| | | | |
|---|---|---|---|
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,869,046 A | 2/1999 | Presta et al. |
| 5,891,996 A | 4/1999 | Mateo de Acosta del Rio et al. |
| 6,004,940 A | 12/1999 | Marasco et al. |
| 6,027,888 A | 2/2000 | Georgiou et al. |
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 9,850,473 B2 | 12/2017 | Wang |
| 10,815,307 B2 | 10/2020 | Yu et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1* | 6/2010 | Wong ................. A61K 39/0011 424/193.1 |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1 | 9/2013 | Papkoff et al. |
| 2014/0363455 A1 | 12/2014 | Stull et al. |
| 2015/0030669 A1 | 1/2015 | Platscher et al. |
| 2015/0087814 A1 | 3/2015 | Wang |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0051672 A1 | 2/2016 | Stewart et al. |
| 2016/0074522 A1 | 3/2016 | Okuda et al. |
| 2016/0102151 A1 | 4/2016 | Wong et al. |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2017/0335281 A1 | 11/2017 | Loew |
| 2018/0028629 A1 | 2/2018 | Yu et al. |
| 2018/0193481 A1 | 7/2018 | Chang et al. |
| 2018/0208915 A1 | 7/2018 | Kawaguchi |
| 2018/0291109 A1 | 10/2018 | Lin et al. |
| 2018/0339061 A1 | 11/2018 | Yu et al. |

FOREIGN PATENT DOCUMENTS

| | | |
|---|---|---|
| EP | 0404097 A2 | 12/1990 |
| EP | 1391213 A1 | 2/2004 |
| EP | 2993182 A1 | 3/2016 |
| JP | 2006-507233 A | 3/2006 |
| JP | 2011524375 A | 9/2011 |
| JP | 2011524417 A | 9/2011 |
| JP | 2012500880 A | 1/2012 |
| JP | 2016500256 A | 1/2016 |
| KR | 10-2012-0014238 A | 2/2012 |
| WO | WO 87/00195 A1 | 1/1987 |
| WO | WO 90/03184 A1 | 4/1990 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/09690 A2 | 6/1992 |
| WO | WO 93/01161 A1 | 1/1993 |
| WO | WO 93/06213 A1 | 4/1993 |
| WO | WO 93/007861 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 94/011026 A2 | 5/1994 |
| WO | WO 95/011010 A1 | 4/1995 |
| WO | WO 96/07754 A1 | 3/1996 |
| WO | WO 96/11711 A1 | 4/1996 |
| WO | WO 96/30347 A1 | 10/1996 |
| WO | WO 96/33735 A1 | 10/1996 |
| WO | WO 96/33978 A1 | 10/1996 |
| WO | WO 96/33980 A1 | 10/1996 |
| WO | WO 96/34096 A1 | 10/1996 |
| WO | WO 96/40210 A1 | 12/1996 |
| WO | WO 97/38983 A1 | 10/1997 |
| WO | WO 98/24893 A2 | 6/1998 |
| WO | WO 98/36772 A1 | 8/1998 |
| WO | WO 98/43960 A1 | 10/1998 |
| WO | WO 99/06378 A1 | 2/1999 |
| WO | WO 99/06396 A1 | 2/1999 |
| WO | WO 99/09016 A1 | 2/1999 |
| WO | WO 99/042130 A1 | 8/1999 |
| WO | WO 2000/41720 A1 | 7/2000 |
| WO | WO 2000/48630 A1 | 8/2000 |
| WO | WO-2000/49412 A1 | 8/2000 |
| WO | WO 2003/015796 A1 | 2/2003 |
| WO | WO 2003/043583 A2 | 5/2003 |
| WO | WO 2003/077945 A1 | 9/2003 |
| WO | WO 2004/011476 A1 | 2/2004 |
| WO | WO 2004/032828 A2 | 4/2004 |
| WO | WO 2005/007197 A2 | 1/2005 |
| WO | WO 2006/105152 A2 | 10/2006 |
| WO | WO 2006/134423 A2 | 12/2006 |
| WO | WO 2007/026190 A2 | 3/2007 |
| WO | 2007047764 A2 | 4/2007 |
| WO | WO 2007/044515 | 4/2007 |
| WO | WO 2009/035494 A2 | 3/2009 |
| WO | WO 2009/126737 A2 | 10/2009 |
| WO | 2010005735 A2 | 1/2010 |
| WO | 2010005735 A3 | 3/2010 |
| WO | WO-2011/156774 A2 | 12/2011 |
| WO | WO 2014/107652 A2 | 7/2014 |
| WO | WO 2014/178195 A1 | 11/2014 |
| WO | WO 2015/143123 A2 | 9/2015 |
| WO | WO 2015/157629 A2 | 10/2015 |
| WO | WO 2015/159118 A2 | 10/2015 |
| WO | WO 2016/026742 A1 | 2/2016 |

(56) References Cited

FOREIGN PATENT DOCUMENTS

| WO | WO 2016/044326 A1 | 3/2016 |
|---|---|---|
| WO | WO 2016/118961 A1 | 7/2016 |
| WO | WO 2016/123593 A1 | 8/2016 |
| WO | 2017004150 A1 | 1/2017 |
| WO | WO 2017/041027 A1 | 3/2017 |
| WO | WO 2017/062792 A1 | 4/2017 |
| WO | 2017185089 A2 | 10/2017 |
| WO | WO 2017/172990 A1 | 10/2017 |
| WO | 2018022933 A1 | 2/2018 |
| WO | WO 2018/022933 A1 | 2/2018 |
| WO | WO 2018/023121 A1 | 2/2018 |
| WO | WO 2018/094414 A1 | 5/2018 |

OTHER PUBLICATIONS

Berenbaum, M. C., What is Synergy?, Pharmacol. Rev. 41(2) :93-141, 1989.
Bliss, C.I., The Calculation of Microbial Assays, Bacterial. Rev. 20:243-258, 1956.
Borisy, Alexis et al., Systematic Discovery of Multicomponent Therapeutics, Proc. Natl. Acad. Sci. 100(13):7977-7982, 2003.
Bremer, E.G. et al., Characterization of a Glycosphingolipid Antigen Defined By The Monoclonal Antibody MBr1 Expressed in Normal and Neoplastic Epithelial Cells of Human Mammary Gland. J Biol Chem 259:14773-14777, 1984.
Brüggemann et al., "Designer mice: the production of human antibody repertoires in transgenic animals," Year in Immunol., 1993, 7:33-40.
Chang et al., "Potent immune-modulating and anticancer effects of NKT cell stimulatory glycolipids," Proc. Natl. Acad. Sci. USA, Jun. 19, 2007, 104(25):10299-10304.
Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.
Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.
Clackson et al., "Making antibody fragments using phage display libraries," Nature, Aug. 15, 1991, 352(6336):624-628.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Fishwild et al., "High-avidity human IgGκ monoclonal antibodies from a novel strain of minilocus transgenic mice," Nature Biotechnol., Jul. 1996, 14(7):845-851.
Fitzgerald, Jonathan et al., Systems Biology and Combination Therapy in the Quest for Clinical Efficacy, Nature Chem. Biol. 2(9):458-466, 2006.
Gilewski, Teresa et al., Immunization of Metastatic Breast Cancer Patients with a Fully Synthetic Globo H Conjugate: A Phase I Trial, Proc Natl Acad Sci USA 98:3270-3275, 2001.
Greco, William et al., The Search for Synergy: A Critical Review From a Response Surface Perspective, Pharmacol. Rev. 47(2) :331-385, 1995.
Hammerling et al., in: Monoclonal Antibodies and T-Cell Hybridomas 563-681, 1981.
Harris, "Production of humanized monoclonal antibodies for in vivo imaging and therapy," Biochem. Soc. Transactions, Nov. 1995, 23(4):1035-1038.
Huang, Cheng-Yuan et al., Carbohydrate Microarray for Profiling the Antibodies Interacting with Globo H Tumor Antigen, Proc Natl Acad Sci, 103:15-20, 2006.
Hurle et al., "Protein engineering techniques for antibody humanization," Curr. Opin. Biotechnol., Aug. 1994, 5(4):428-433.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.

Jakobovits et al., "Germ-line transmission and expression of a human-derived yeast artificial chromosome," Nature, Mar. 18, 1993, 362(6417):255-258.
Jones et al., "Replacing the complementarity-determining regions in a human antibody with those from a mouse," Nature, May 29-Jun. 4, 1986, 321(6069):522-525.
Köhler et al., "Continuous cultures of fused cells secreting antibody of predefined specificity," Nature, Aug. 7, 1975, 256(5517):495-497.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Lee et al., "Bivalent antibody phage display mimics natural immunoglobulin," J. Immunol. Methods, Jan. 2004, 284(1-2): 119-132.
Lee et al., "High-affinity human antibodies from phage-displayed synthetic Fab libraries with a single framework scaffold," J. Mol. Biol., Jul. 23, 2004, 340(5):1073-1093.
Lonberg et al., "Antigen-specific human antibodies from mice comprising four distinct genetic modifications," Nature, Apr. 28, 1994, 368(6474):856-859.
Lonberg et al., "Human antibodies from transgenic mice," Int. Rev. Immunol., 1995, 13(1):65-93.
Marks et al., "By-passing immunization. Human antibodies from V-gene libraries displayed on phage," J. Mol. Biol., Dec. 5, 1991, 222(3):581-597.
Marks et al., "By-passing immunization: Building high affinity human antibodies by chain shuffling," Nature Biotechnology, Jul. 1992, 10(7):779-783.
Morrison et al., "Chimeric human antibody molecules: mouse antigen-binding domains with human constant region domains," Proc. Natl. Acad. Sci. U.S.A., Nov. 1984, 81(21):6851-6855.
Morrison, "Immunology. Success in specification," Nature, Apr. 28, 1994, 368(6474):812-813.
Neuberger, "Generating high-avidity human Mabs in mice," Nature Biotechnol., Jul. 1996, 14(7):826.
Nicolaou et al., "Calicheamicin $\Theta^I_1$: A rationally designed molecule with extremely potent and selective DNA cleaving properties and apoptosis inducing activity," Angew. Chem. Intl. Ed. Engl., Feb. 1, 1994, 33(2):183-186.
Pegram, Mark et al., Inhibitory Effects of Combinations of HER-2/neu Antibody and Chemotherapeutic Agents Used for Treatment of Human Breast Cancers, Oncogene 18:2241-2251, 1999.
Pegram, Mark et al., Rational Combinations of Trastuzumab With Chemotherapeutic Drugs Used in the Treatment of Breast Cancer, J. of the Nat. Cancer Inst. 96(10):739-749, 2004.
Presta, "Antibody engineering," Curr. Opin. Struct. Biol., Aug. 1992, 2(4):593-596.
Ragupathi, Govindaswami et al., Immunization of Mice with a Fully Synthetic Globo H Antigen Results in Antibodies against Human Cancer Cells: A Combined Chemical—Immunological Approach to the Fashioning of an Anticancer Vaccine, Angew Chem Int, 36(1-2), 125-128, Feb. 1997.
Riechmann et al., "Reshaping human antibodies for therapy," Nature, Mar. 24, 1988, 332(6162):323-327.
Sidhu et al., "Phage-displayed antibody libraries of synthetic heavy chain complementarity determining regions," J. Mol. Biol., Apr. 23, 2004, 338(2):299-310.
Vaswani et al., "Humanized antibodies as potential therapeutic drugs," Ann. Allergy, Asthma Immunol., Aug. 1998, 81(2):105-116, 119.
Wang et al., "Glycan microarray of Globo H and related structures for quantitative analysis of breast cancer," Proc. Natl. Acad. Sci. U.S.A., Aug. 19, 2008, 105(33):11661-11666.
Abrahmsén et al., "Analysis of signals for secretion in the staphylococcal protein A gene," EMBO J., Dec. 30, 1985, 4(13B):3901-3906.
Allen, P. Z. et al., Immunochemical Studies on a Sophorosyl-Azoprotein Conjugate, Biochemistry, 1967, 6(10), 3029-3036.
Arié et al., "Chaperone function of FkpA, a heat shock prolyl isomerase, in the periplasm of Escherichia coli," Mol. Microbiol., Jan. 2001, 39(1):199-210.

(56) References Cited

OTHER PUBLICATIONS

Arigi, Emma, et al. "Design of a covalently bonded glycosphingolipid microarray." Glycoconjugate Journal 29.1 (2012): 1-12.
Avery, Oswald et al., Chemo-Immunological Studies on Conjugated Carbohydrate-Proteins, J. Exp. Med., 1929, 50, 533-550.
Bachmann, Cellular and Molecular Biology, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas, C.F. et al., "Semisynthetic combinatorial antibody libraries: a chemical solution to the diversity problem" Proc. Natl. Acad. Sci. USA, May 15, 1992, 89(10): 4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Bergman, Jan, and Lennart Venemalm. "Efficient synthesis of 2-chloro-, 2-bromo-, and 2-iodoindole." The Journal of Organic Chemistry 57.8 (1992): 2495-2497.
Bertozzi, CR et al., Glycans in Cancer and Inflammation-Potential for Therapeutics and Diagnostics, Nat Rev Drug Discovery, 2005, 4, 477-488.
Bhaskar, Vinay, et al. "E-selectin up-regulation allows for targeted drug delivery in prostate cancer." Cancer Research 63.19 (2003): 6387-6394.
Bird, R.E., et al., "Single-chain antigen-binding proteins" Science Oct. 21, 1988; 242(4877):423-426.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Bosse, Folkert et al., Linear Synthesis of the Tumor-Associated Carbohydrate Antigens Globo-H, SSEA-3, and Gb3, J Org Chem. 67(19):6659-70, 2002.
Bothmann et al., "The periplasmic *Escherichia coli* peptidylprolyl cis,trans-isomerase FkpA. I. Increased functional expression of antibody fragments with and without cis-prolines," J. Biol. Chem., Jun. 2, 2000, 275(22):17100-17105.
Bowie, JU et al., Deciphering the Message in Protein Sequences: Tolerance to Amino Acid Substitutions, Science, 247: 1306-1310 (1990).
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Carter et al., "High level *Escherichia coli* expression and production of a bivalent humanized antibody fragment," Nature Biotechnology, Feb. 1992, 10(2):163-167.
Carter et al., "Humanization of an anti-p185HER2 antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J. Bio. Chem., Jul. 9, 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.
Cheung, Sarah et al., Stage-Specific Embryonic Antigen-3 (SSEA-3) and ß3GalT5 are cancer specific and Significant Markers for Breast Cancer Stem Cells, PNAS, Jan. 26, 2016, vol. 113, No. 4, pp. 960-965.
Chothia et al., "Canonical structures for the hypervariable regions of immunoglobulins," J. Mol. Biol., Aug. 20, 1987, 196(4):901-917.
Chuang, Po-Kai, et al. "Signaling pathway of globo-series glycosphingolipids and ß1, 3-galactosyltransferase V (ß3GalT5) in breast cancer." Proceedings of the National Academy of Sciences 116.9 (2019): 3518-3523.
ClinicalTrials.gov [Internet]. Bethesda (MD): National Library of Medicine (US). Jan. 24, 2012-. Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.
Clynes, Raphael, et al. "Fc receptors are required in passive and active immunity to melanoma." Proceedings of the National Academy of Sciences 95.2 (1998): 652-656.
Colman, P.M., "Effects of amino acid sequence changes on antibody-antigen interactions," Research in Immunology 145:33-36, 1994.
Cunningham et al., "High-resolution epitope mapping of hGH-receptor interactions by alanine-scanning mutagenesis," Science, Jun. 2, 1989, 244(4908):1081-1085.
Cuzick, J., et al. "Overview of the main outcomes in breast-cancer prevention trials." The Lancet 361.9354 (2003): 296-300.
Danishefsky, Samuel J., et al. "Development of Globo-H cancer vaccine." Accounts of Chemical Research 48.3 (2015): 643-652.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Doronina, Svetlana O., et al. "Development of potent monoclonal antibody auristatin conjugates for cancer therapy." Nature Biotechnology 21.7 (2003): 778-784.
Eller, Chelcie et al., Human Cancer Antigen Globo H Is a Cell-Surface Ligand for Human Ribonuclease 1, ACS Central Science. vol. 1, p. 181-190, Jul. 13, 2015.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Evans, T. R. J., and S. B. Kaye. "Vaccine therapy for cancer—fact or fiction?" Q J Med 92.6 (1999): 299-307.
Extended European Search Report, Application No. 15842660.1, dated Mar. 12, 2018, 9 pages.
Extended European Search Report from corresponding European App. No. 16843131.0, dated Feb. 14, 2019, 13 Pages.
Feng, Li. "Probing lipid-protein interactions using lipid microarrays." Prostaglandins & other lipid mediators 77.1-4 (2005): 158-167.
Fielder, R. J. et al., An Immunogenic Polysaccharide-Protein Conjugate, J. Immunol., 1970, 105(1), 265-267.
Francisco, Joseph A., et al. "cAC10-vcMMAE, an anti-CD30-monomethyl auristatin E conjugate with potent and selective anti-tumor activity." Blood 102.4 (2003): 1458-1465.

(56) References Cited

OTHER PUBLICATIONS

Galfrè et al., "Preparation of monoclonal antibodies: strategies and procedures," Methods Enzymol., 1981, 73(Pt B):3-46.
Gazzano-Santoro, Hélène, et al. "A non-radioactive complement-dependent cytotoxicity assay for anti-CD20 monoclonal antibody." Journal of Immunological Methods 202.2 (1997): 163-171.
Gijsen, H.J. et al., Recent Advances in the Chemoenzymatic Synthesis of Carbohydrates and Carbohydrate Mimetics, Chem. Rev., 96, 443-473, 1996.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2nd ed., Chapter 3: Production of Monoclonal Antibodies, 1986, pp. 59-103, Academic Press, London.
Goebel, Walther et al., Chemo-immunological Studies on Conjugated Carbohydrate-Proteins, J. Exp. Med., 1929, 50, 521-531.
Gonnet, GH et al., Exhaustive Matching of the Entire Protein Sequence Database, Science 256: 1443-1445 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Grant, Oliver C., et al. "Presentation, presentation, presentation! Molecular-level insight into linker effects on glycan array screening data." Glycobiology 24.1 (2014): 17-25.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in *Escherichia coli*," J. Immunol., Jun. 1, 1994, 152(11):5368-5374.
Guss et al., "Structure of the IgG-binding regions of streptococcal protein G," EMBO J., Jul. 1986, 5(7):1567-1575.
Hakomori et al., "Glycosphingolipid antigens and cancer therapy," Chem. & Biol., Feb. 1997, 4(2):97-104.
Hakomori, Sen-Itiroh, Tumor-associated carbohydrate antigens defining tumor malignancy: Basis for development of and-cancer vaccines, 2001, Advances in Experimental Medicine and Biology. 491 :369-402.
Ham, Richard et al., Media and Growth Requirements, Meth. Enz 58, 44-93 (1979).
Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark 1. "Keyhole limpet hemocyanin (KLH): a biomedical review." Micron 30.6 (1999): 597-623.
Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.

Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
Huston, James et al., "Protein Engineering of Antibody Binding Sites: Recovery of Specific Activity in an Anti-Digoxin Single-Chain Fv Analogue Produced in *Escherichia Coli*" Proc. Natl. Acad. Sci. USA, 1988, 85:5879-5883.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion of the International Searching Authority, from corresponding International Patent Application No. PCT/US16/50252, dated Nov. 17, 2016, 12 Pages.
International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report/Written Opinion dated Oct. 31, 2017 in counterpart PCT Application No. PCT/US2017/044244, 13 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
International Search Report/Written Opinion dated Oct. 18, 2019 in counterpart application PCT/US2019/035168, 13 pages.
International Search Report dated Dec. 3, 2019 in counterpart application PCT/US2019/039414, 5 pages.
Jackson et al., "In vitro antibody maturation: Improvement of a high affinity, neutralizing antibody against IL-1β," J. Immunol., Apr. 1, 1995, 154(7):3310-3319.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones, "Analysis of polypeptides and proteins," Adv. Drug Delivery Rev., Jan.-Apr. 1993, 10(1):29-90.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi, Reiji, et al. "Stage-specific embryonic antigens (SSEA-3 and-4) are epitopes of a unique globo-series ganglioside isolated from human teratocarcinoma cells." EMBO Journal 2.12 (1983): 2355-2361.

(56) References Cited

OTHER PUBLICATIONS

Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.

Klussman, Kerry, et al. "Secondary mAb- vcMMAE conjugates are highly sensitive reporters of antibody internalization via the lysosome pathway." Bioconjugate chemistry 15.4 (2004): 765-773.

Koeller, Kathryn et al., Enzymes for Chemical Synthesis, Nature, 409, 232-240, 2001.

Komenaka, Ian, Heidi Hoerig, and Howard L. Kaufman. "Immunotherapy for melanoma." Clinics in Dermatology 22.3 (2004): 251-265.

Kontermann, "Intrabodies as therapeutic agents," Methods, Oct. 2004, 34(2):163-170.

Kostelny et al., "Formation of a bispecific antibody by the use of leucine zippers," J. Immunol., Mar. 1, 1992, 148(5):1547-1553.

Kozbor, "A human hybrid myeloma for production of human monoclonal antibodies," J. Immunol., Dec. 1984, 133(6):3001-3005.

Krainer, Florian et al., An Updated View on Horseradish Peroxidases: Recombinant Production and Biotechnological Applications, Applied Microbiology and Biotechnology, vol. 99, p. 1611-1625, Jan. 11, 2015.

Kufer, Peter, et al. "A revival of bispecific antibodies." Trends in biotechnology 22.5 (2004): 238-244.

Lee et al. "Immunogenicity study of Globo H analogues with modification at the reducing or nonreducing end of the tumor antigen" Journal of the American Chemical Society, (2014) 136(48), 16844-16853.

Lehninger, Biochemistry: The Molecular Basis of Cell Structure and Function, 2nd ed., 1975, pp. 73-75, Worth Publishers, New York.

Leung et al., "A method for random mutagenesis of a defined DNA segment using a modified polymerase chain reaction," Technique—A Journal of Methods in Cell and Molecular Biology, Aug. 1989, 1(1):11-15.

Liang, Pi-Hui, et al. "Quantitative Microarray Analysis of Intact Glycolipid-CD1d Interaction and Correlation with Cell-Based Cytokine Production." Journal of the American Chemical Society 130.37 (2008): 12348-12354.

Lindmark et al., "Binding of immunoglobulins to protein A and immunoglobulin levels in mammalian sera," J. Immunol. Meth., Aug. 12, 1983, 62(1):1-13.

Liu et al., "Eradication of large colon tumor xenografts by targeted delivery of maytansinoids," Proc. Natl., Acad. Sci. U.S.A., Aug. 6, 1996, 93(16):8618-8623.

Liu, Gui, et al. "QS-21 structure/function studies: effect of acylation on adjuvant activity." Vaccine 20.21-22 (2002): 2808-2815.

Livingston, Philip, "Augmenting the immunogenicity of carbohydrate tumor antigens" Seminars in Cancer Biology, Cancer Biol, 6(6):357-366, 1995.

Lloyd, Kenneth, "Tumor Antigens Known to be Immunogenic in Man" in Specific Immunotherapy of Cancer with Vaccines, 1993, 690, 50-58.

Lode et al., "Targeted therapy with a novel enediyene antibiotic calicheamicin θI1 effectively suppresses growth and dissemination of liver metastases in a syngeneic model of murine neuroblastoma," Cancer Res., Jul. 15, 1998, 58(14):2925-2928.

Lou, et al., Stage-specific embryonic antigent-4 as a potential therapeutic target in glioblastoma multiforms and other cancers. Proc Natl Acad Sci USA 2014, 111(7):2482-7.

Lucas, A.H. et al., Carbohydrate Moieties as Vaccine Candidates: Meeting Summary, Vaccine, vol. 28(4), Jan. 2010, pp. 1121-1131.

Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.

Mao, Weiguang, et al. "EphB2 as a therapeutic antibody drug target for the treatment of colorectal cancer." Cancer Research 64.3 (2004): 781-788.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Martineau, R.S. et al., Immunochemical Studies on a Panosyl-Azoprotein conjugate, Immunochemistry, vol. 8, 705-718, 1971.

Mather et al., "Culture of testicular cells in hormone-supplemented serum-free medium," Annals N.Y. Acad. Sci., 1982, 383:44-68.

Mather, "Establishment and characterization of two distinct mouse testicular epithelial cell lines," Biol. Reprod., Aug. 1980, 23(1):243-252.

Matsuda, F. et al., "Structure and physical map of 64 variable segments in the 3' 0.8-megabase region of the human immunoglobulin heavy-chain locus." Nature Genet., 1993, 3: 88-94.

McCafferty et al., "Phage antibodies: Filamentous phage displaying antibody variable domains," Nature, Dec. 6, 1990, 348:552-554.

Menard S et al., Generation of Monoclonal Antibodies Reacting with Normal and Cancer Cells of Human Breast, Cancer Res 43: 1295-1300, 1983.

Miller, Kathy, et al. "Design, construction, and in vitro analyses of multivalent antibodies." The Journal of Immunology 170.9 (2003): 4854-4861.

Milstein, C & Cuello, AC, Hybrid Hydridomas and their use in immunohistochemistry, Nature 305, 537-540, Oct. 1983.

Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.

Munson et al., "LIGAND: a versatile computerized approach for characterization of ligand-binding systems," Anal. Biochem., Sep. 1, 1980, 107(1):220-239.

Neuberger et al., "Recombinant antibodies possessing novel effector functions," Nature, Dec. 13-19, 1984, 312(5995):604-608.

Niculescu-Duvaz et al., "Antibody-directed enzyme prodrug therapy (ADEPT): A review," Adv. Drg. Del. Rev., Jul. 7, 1997, 26(2-3):151-172.

Nikula, Kristen et al., Animal Models of Chronic Bronchitis and Their Relevance to Studies of Particle-Induced Disease, Inhal. Toxicol. 4(12): 123-153, 2000.

Office Action issued in corresponding Taiwan patent application No. 103131876, dated Dec. 26, 2016, 7 pages.

Orlandi et al., "Cloning immunoglobulin variable domains for expression by the polymerase chain reaction," Proc. Natl. Acad. Sci. U.S.A., May 1989, 86(10):3833-3837.

Ørum et al., "Efficient method for constructing comprehensive murine Fab antibody libraries displayed on phage." Nucleic Acids Res., Sep. 25, 1993, 21(19):4491-4498.

Oxenius, Annette, et al. "CpG-containing oligonucleotides are efficient adjuvants for induction of protective antiviral immune responses with T-cell peptide vaccines." Journal of Virology 73.5 (1999): 4120-4126.

Papanastassiou et al., "The potential for efficacy of the modified (ICP 34.5-) herpes simplex virus HSV1716 following intratumoural injection into human malignant glioma: a proof of principle study," Gene Therapy, Mar. 2002, 9(6):398-406.

(56) References Cited

OTHER PUBLICATIONS

Paul, William E. "Structure and Function of Immunoglobulins, Fundamental Immunology." Chapter 9 (1993), 3rd Edition: 292-295.
Pearson, William, Using the FASTA Program to Search Protein and DNA Sequence Databases, Methods Mol. Biol. 243:307-331, 1994.
Plückthun, "Mono- and bivalent antibody fragments produced in *Escherichia coli*: Engineering, folding and antigen binding," Immunol. Rev., Dec. 1992, 130:151-188.
Plückthun, Handbook of Experimental Pharmacology, vol. 113: The Pharmacology of Monoclonal Antibodies, Chapter 11: Antibodies from *Escherichia coli*, Rosenberg et al., eds., 1994, pp. 269-315, Springer-Verlag, Berlin.
Presta et al., "Humanization of an antibody directed against IgE," J. Immunol., Sep. 1, 1993, 151(5):2623-2632.
Presta et al., "Humanization of an anti-vascular endothelial growth factor monoclonal antibody for the therapy of solid tumors and other disorders," Cancer Res., Oct. 15, 1997, 57(20):4593-4599.
Presta, Leonard G. "Antibody engineering." Current Opinion in Biotechnology 3.4 (1992): 394-398.
Proba et al., "Functional antibody single-chain fragments from the cytoplasm of *Escherichia coli*: influence of thioredoxin reductase (TrxB)," Gene, Jul. 4, 1995, 159(2):203-207.
Queen, Cary et al., A Humanized Antibody that Binds to the Interleukin 2 Receptor, Proc Natl Acad Sci., 86: 10029-10033 (1989).
Ragupathi, Govindaswami, et al. "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm." Glycoconjugate Journal 15.3 (1998): 217-221.
Ragupathi, Govindaswami, et al. "Constructing an adenocarcinoma vaccine: Immunization of mice with synthetic KH-1 nonasaccharide stimulates anti-KH-1 and anti-Ley antibodies." International Journal of Cancer 99.2 (2002): 207-212.
Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Rowland et al., "Drug localisation and growth inhibition studies of vindesine-monoclonal anti-CEA conjugates in a human tumour xenograft," Cancer Immunol. Immunother., 1986, 21(3):183-187.
Rüde, Erwin et al., Synthesis of the N-carboxy-α-amino Acid Anhydrides of Several O-acetylated Serine Glycosides, Carbohydr. Research, 1968, 8(2), 219-232.
Rudikoff, Stuart, et al. "Single amino acid substitution altering antigen-binding specificity." Proceedings of the National Academy of Sciences 79.6 (1982): 1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.
Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.
Search Report issued in corresponding Taiwan patent application No. 103131876, prepared Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Siebenlist et al., "*E. coli* RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in *Escherichia coli*: Rapid and efficient production of aglycosylated antibodies," J. Immunol. Methods, May 1, 2002, 263(1-2): 133-147.
Sims et al., "A humanized CD 18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Sonderstrup, Grete, Development of Humanized Mice as a Model of Inflammatory Arthritis, Springer Sem. Immunopathol. 25: 35-45, 2003.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers of Cytotoxic Agents In Cancer Therapy: A Review," in Monoclonal Antibodies '84: Biological And Clinical Applications, A. Pinchera et al. (Ed.s), pp. 475-506.
Tomlinson, I.M. et al., "The repertoire of human germline VH sequences reveals about fifty groups of VH segments with different hypervariable loops" J. Mol. Biol., Oct. 5, 1992, 227(3): 776-798.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')3 derivatives that use cooperative signaling via the TCR/CD3 complex and CD2 to activate and redirect resting cytotoxic T cells," J. Immunol., Jul. 1, 1991, 147(1):60-69.
Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Verhoeyen et al., "Reshaping human antibodies: grafting an antilysozyme activity," Science, Mar. 25, 1988, 239(4847):1534-1536.

(56) References Cited

OTHER PUBLICATIONS

Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glyco sphingolipid analogues for preparation of glycoconjugate arrays." Organic & Biomolecular Chemistry 3.2 (2005): 309-315.
Ward et al., "Binding activities of a repertoire of single immunoglobulin variable domains secreted from *Escherichia coli*," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wilen et al., "Strategies in optical resolutions," Tetrahedron, 1977, 33(21):2725-2736.
Williams, S.C. and Winter, G. "Cloning and sequencing of human immunoglobulin Vλ gene segments" Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Wymer, Nathan et al., Enzyme-Catalyzed Synthesis of Carbohydrates, Curr. Opin. Chem. Biol., 4, 110-119, 2000.
Yaniv, Moshe, Enhancing Elements for Activation of Eukaryotic Promoters, Nature 297: 17-18, 1982.
Yansura et al., "Nucleotide sequence selection for increased expression of heterologous genes in *Escherichia coli*," Methods: A Companion to Methods in Enzymol., Aug. 1992, 4(2):151-158.
Yelton et al., "Affinity maturation of the BR96 anti-carcinoma antibody by codon-based mutagenesis." J. Immunol., Aug. 15, 1995, 155(4):1994-2004.
Zhang et al., "Selection of tumor antigens as targets for immune attack using immunohistochemistry: I. Focus on gangliosides," Int. J. Cancer, Sep. 26, 1997,73(1):42-49.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Zhu, Jianglong et al., From Synthesis to Biologies: Preclinical Data on a Chemistry Derived Anticancer Vaccine, J. Am. Chem. Soc. 131(26):9298-9303, 2009.
Eller, Chelcie et al., "Affinity of monoclonal antibodies for Globo-series glycans," Carbohydrate Research, (2014), 397, 1-6.
Gebauer, Wolfgang et al., "Keyhole Limpet Hemocyanin Type 2 (KLH2): Detection and Immunolocalization of a Labile Functional Unit h," J Structrual Biology, vol. 128, p. 280-286, 1999.
Gilewski, T et al., "Immunization of of metastatic breast cancer patients with a fully synthetic globo H conjugate: A phase I trial," PNAS, 98(6), pp. 3270-3275, Mar. 13, 2001.
Lou, Yi-Wei et al., "Stage-specific embryonic antigen-4 as a potential therapeutic target in glioblastoma multiforme and other cancers," PNAS, (2014), 111(7): 2482-2487.
Sasikumar et al., "Small-Molecule Immune Checkpoint INhibitors Targeting PD-1/PD-L1 and Other Emerging Checkpoint Pathways," BioDrugs, 2018, 32:481-497.
Blast alignment of GenBank AN126084.1 and SEQ ID No. 1 (downloaded Nov. 20, 2020). (Year: 2020).
Non-Final Office Action issued in U.S. Appl. No. 14/855,260 dated Jul. 27, 2021.
Final Office Action issued in U.S. Appl. No. 16/454,750 dated May 27, 2021.
First Examination Report dated Jul. 5, 2021 in India Patent Application No. 201717013151.
Substantive Examination Report, Office Paper No. 7, issued in Philippines Application No. 1-2017-500478 dated Oct. 21, 2020.
Substantive Examination Report, Office Paper No. 9, issued in Philippines Application No. 1-2017-500478 dated Jun. 10, 2021.
International Search Report dated Mar. 24, 2022, in International Patent Publication No. WO 2022/072513.
Lin, Yuan et al., "Improved affinity of a chicken single-chain antibody to avian infectious bronchitis virus by site-directed mutagenesis of complementarity-determining region H3", African Journal of Biotechnology, vol. 10(79), pp. 18294-18302, Dec. 12, 2011.
Mariuzza, R.A. et al., "The Structural Basis of Antigen-Antibody Recognition", Ann. Rev. Biophys. Chem, 1987, vol. 16, pp. 139-159.
McCarthy, Barry J., et al."Altering the find specificity of an anti-Legionella single chain antibody by a single amino acid insertion", Journal of Immunological Methods, 2001, vol. 251, pp. 137-149.
Ragupathi, G., et al., "A fully synthetic globo H carbohydrate vaccine induces a focused humoral response in prostate cancer patients: a proof of principle," Angewandte Chemie International Edition 38.4 (1999): 569-566. Feb. 24, 1999.
Genbank: CAG28308.1, May 13, 2004.
Genbank: CAG28309.2, Nov. 26, 2013.
NCT01516307—Trial of Active Immunotherapy with Globo H-KLH (OPT-822) in Metastatic Breast Cancer Subjects. Full Text Review ClinicalTrials.gov. Jan. 2012. (https://clinicaltrials.gov/ct2/show/NCT01516307).
Pravetoni, M et al. "Structurally distinct nicotine immunogens elicit antibodies with non-overlapping specificities," Biochem Pharmacol, Feb. 15, 2012, vol. 83. No. 4, 543-550. 19 pages.
Sledzinska, Anna et al."Negative immune checkpoints on T lymphocytes and their relevance to cancer mmunotherapy," Molecular Oncology, 2015, vol. 9, pp. 1936-1965 (30 pages).
Wang, Z.-G. et al., "Polyclonal antibodies from patients immunized with a globo H-keyhole limpet hemocyanin Vaccine: Isolation, quantification, and characterization of immune responses by using totally synthetic immobilized tumor antigens," PNAS, Mar. 14, 2000, vol. 97, No. 6, pp. 2719-2724.

\* cited by examiner

Fig. 10

| Subject No. | Visit | Lesion Category | Date of Assessment | Status | Method | Organ | Response |
|---|---|---|---|---|---|---|---|
| 001 | Screening | TARGET | 2015-03-18 | Mass | | | |
| | | NON-TARGET | 2015-03-18 | Mass | | | |
| | Visit 1 | TARGET | 2015-10-01 | Mass | | | |
| | | NON-TARGET | 2015-10-01 | Mass | | | |
| | | New | 2015-10-01 | | | | |
| | | Overall | 2015-10-01 | | | | |

| Subject No. | Visit | Lesion Category | Date of Assessment | Status | Method | Organ | Response |
|---|---|---|---|---|---|---|---|
| 010 | Screening | TARGET | 2015-01-06 | None | | | |
| | | NON-TARGET | 2015-01-06 | PRESENT | CT SCAN | ILLEGIBLE | |
| | Visit 2 | TARGET | 2015-08-17 | None | | | SD |
| | | NON-TARGET | 2015-08-17 | PRESENT | CT SCAN | ILLEGIBLE | SD |
| | | NEW | 2015-08-17 | | | | N |
| | | Overall | 2015-08-17 | | | | SD |

Fig. 14
Step 1: Thaw 30 min (Vial 1 & 2).
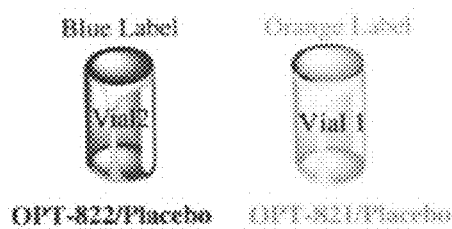
OPT-822/Placebo   OPT-821/Placebo
Step 2: Transfer 0.5 ml from Vial 2 to Vial 1
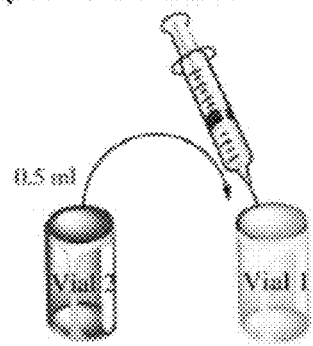
0.5 ml
Step 3: Gently mix Vial 1 by gently inverting the vial 4-5 times.
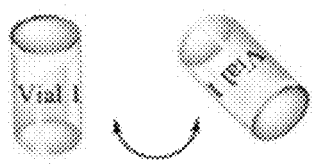
Step 4: Withdraw 0.8 ml from Vial 1 for subject injection within 2 hour.
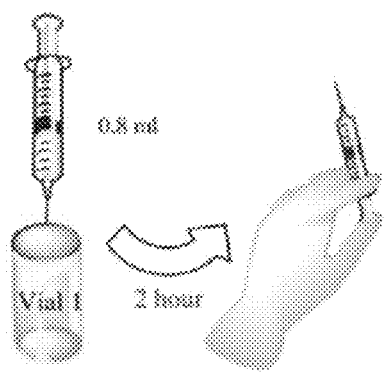
0.8 ml    2 hour

CANCER IMMUNOTHERAPY BY IMMUNE ACTIVATION OR IMMUNE MODULATION VIA GLOBO SERIES ANTIGENS

CROSS-REFERENCE TO RELATED APPLICATIONS

This application claims the priority of U.S. Provisional Patent Applications No. 62/326,623 (filed Apr. 22, 2016), 62/343,530 (filed May 31, 2016), 62/345,755 (filed Jun. 4, 2016) and 62/381,875 (filed Aug. 31, 2016). The entirety of the aforementioned application is incorporated herein by reference.

FIELD OF THE INVENTION

This invention relates to methods for immunotherapy of a cancer patient comprising administering to the patient vaccines against Globo series antigens.

BACKGROUND OF THE INVENTION

The carbohydrate antigen Globo H (Fucα1→2 Galβ1→3 GalNAcβ1→3 Galα1→4 Galβ1→4 Glc) was first isolated as a ceramide-linked Glycolipid and identified in 1984 by Hakomori et al. from breast cancer MCF-7 cells. (Bremer E G, et al. (1984) J Biol Chem 259:14773-14777). Further studies with anti-Globo H monoclonal antibodies showed that Globo H was present on many other cancers, including prostate, gastric, pancreatic, lung, ovarian and colon cancers and only minimal expression on luminal surface of normal secretory tissue which is not readily accessible to immune system. (Ragupathi G, et al. (1997) Angew Chem Int Ed 36:125-128). In addition, it has been established that the serum of breast cancer patient contains high level of anti-Globo H antibody. (Gilewski T et al. (2001) Proc Natl Acad Sci USA 98:3270-3275; Huang C- Y, et al. (2006) Proc Natl Acad Sci USA 103:15-20; Wang C-C, et al. (2008) Proc Natl Acad Sci USA 105(33):11661-11666). Patients with Globo H-positive tumors showed a shorter survival in comparison to patients with Globo H-negative tumors. (Chang, Y-J, et al. (2007) Proc Natl Acad Sci USA 104(25):10299-10304). These findings render Globo H, a hexasaccharide epitope, an attractive tumor marker and a feasible target for cancer vaccine development.

SUMMARY OF THE INVENTION

Aspects and embodiments of the present disclosure provide methods for treating a subject afflicted with cancer by immunotherapy comprising administering to a subject in need thereof a Globo series antigens targeting immunogenic agent (e.g., OBI-822) useful for inducing/modulating an immune response (IgG and/or IgM). The aforementioned method comprises improving the survival (including overall survival and/or progression free survival) by modulating Globo series antigens interaction, such that survival of the subject is improved. In one aspect, the Globo series antigens targeting immunogenic agent is, for example, OBI-822, as described in PCT patent application publication numbers: WO2015159118A2 and WO2016044326A1; OBI-821 and OBI-834, as described in PCT patent application publication number: WO2014107652A2. These applications disclose immunogenic/therapeutic compositions including Globo H-KLH glycoconjugates (OBI-822) and/or therapeutic adjuvants (OBI-821/OBI-834), as well as methods of making and using the same to treat proliferative diseases such as cancer. The therapeutic compositions are in part envisaged to act as cancer vaccines for boosting the body's natural ability to protect itself through the immune system from dangers posed by damaged or abnormal cells such as cancer cells.

OBI-822 is Fucα(1→2)Galβ(1→3)GalNAcβ(1→3)Galα(1→4)Galβ(1→4)Gluβ(1-O-ethylhydrazyl-1-carbo nyl-cyclohexyl-4-(methyl-N-maleimido)-3-(thiobutyl-imidyl)-Keyhole Limpet Hemocyanin (KLH), prepared by the process described herein which includes storage of a thiolated KLH intermediate under inert gas.

OBI-821 saponins are naturally occurring glycosides, extracted in high purify from the bark of the Quillaja saponaria Molina tree, by high pressure liquid chromatography (HPLC), low pressure liquid silica chromatography, and hydrophilic interactive chromatography (HILIC). In certain embodiments, OBI-821 saponin comprise at least one isolated compound of formula I as follows:

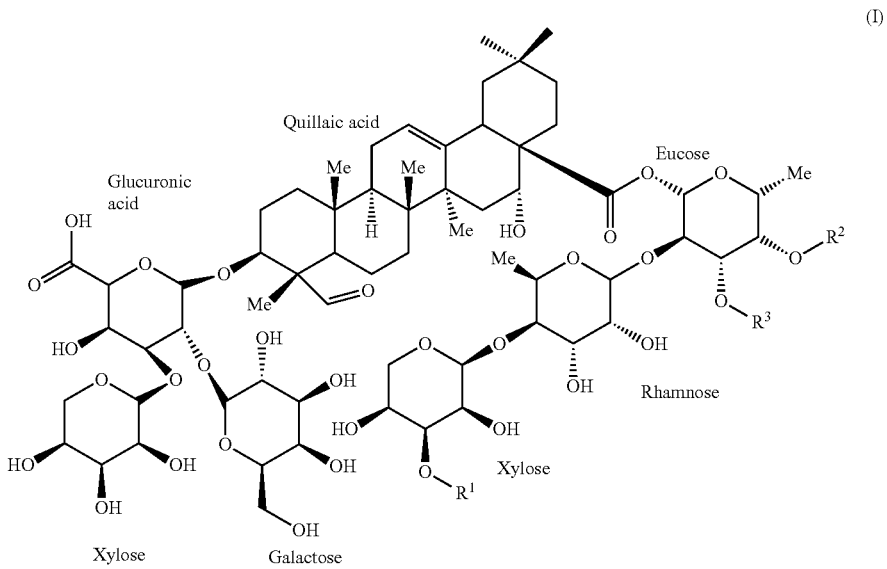

(I)

wherein

R1 is β-D-Apiose or β-D-Xylose; and

R2 and R3 are independently H, alkyl,

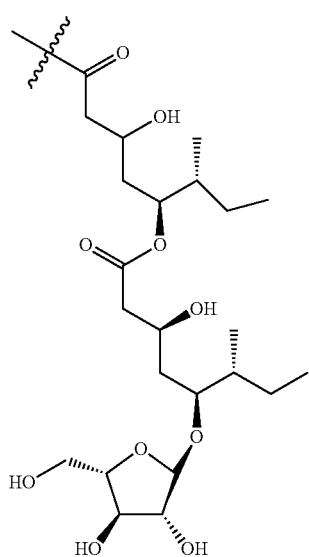

(fatty acyl moiety for Compound 1989), or

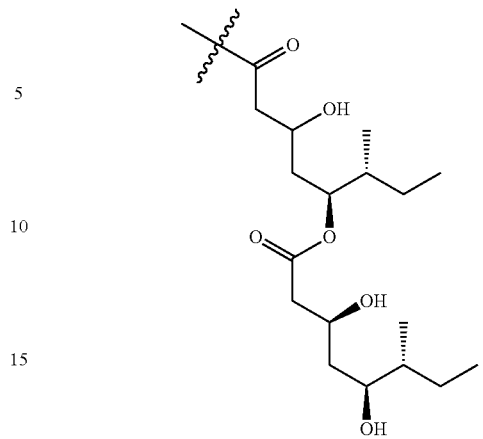

(fatty acyl moiety for Compound 1857).

OBI-821 saponin can also comprise an isolated compound of formula I, wherein
- (i) $R^1$ is β-D-Apiose, $R^2$ is the fatty acyl moiety for the 1989 compound depicted above, and $R^3$ is H (1989 compound V1A);
- (ii) $R^1$ is β-D-Apiose, $R^2$ is H, and $R^3$ is the fatty acyl moiety fatty acyl moiety for the 1989 compound depicted above (1989 compound V1B);
- (iii) $R^1$ is β-D-Xylose, $R^2$ is the fatty acyl moiety fatty acyl moiety for the 1989 compound depicted above, and $R^3$ is H (1989 compound V2A); or
- (iv) $R^1$ is β-D-Xylose, $R^2$ is H, and $R^3$ is the fatty acyl moiety fatty acyl moiety for the 1989 compound depicted above (1989 compound V2B). Collectively, 1989 compound V1A, 1989 compound V1B, 1989 compound V2A and 1989 compound V2B are called "1989 compounds mixture."

Table 9 summarizes the functional groups of 1989 compounds and the mole % of each 1857 compound in the 1857 compounds mixture.

Table 9.

TABLE 9

| Mole % | $R^1$ | $R^2$ | $R^3$ |
|---|---|---|---|
| 1989 Compound V1A 64.5% | β-D-Apiose | (structure) | H |

TABLE 9-continued
| Mole % | R$^1$ | R$^2$ | R$^3$ |
| --- | --- | --- | --- |
| 1989 Compound V1B 1.5% | β-D-Apiose | H | |
| 1989 Compound V2A 33.3% | β-D-Xylose | | H |
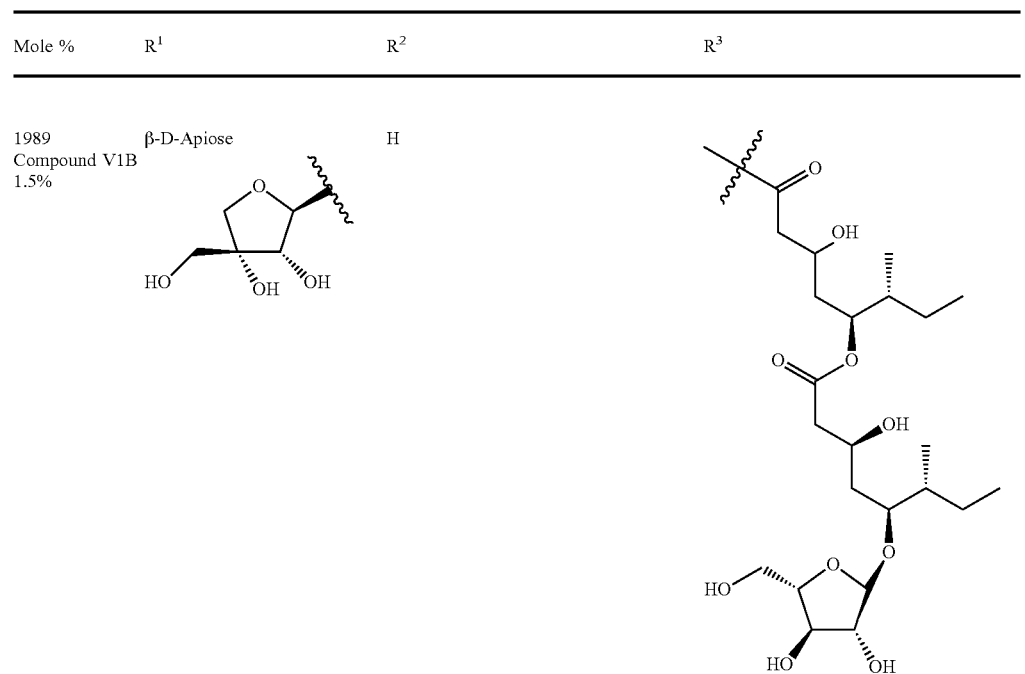
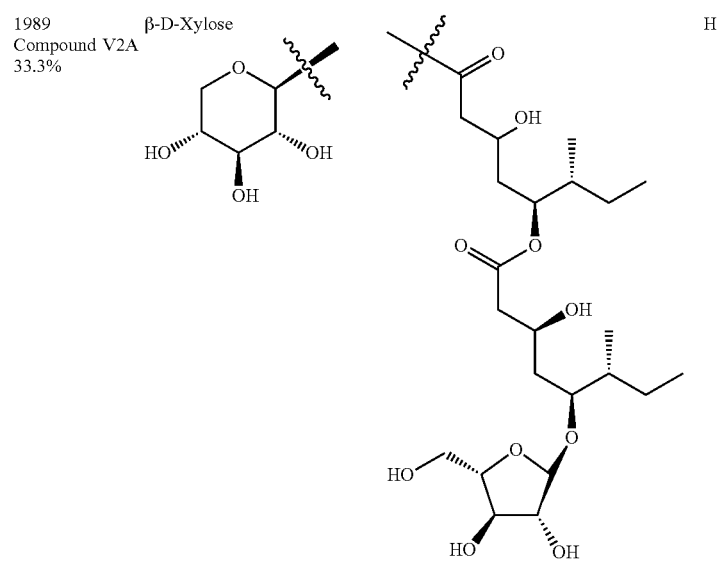

TABLE 9-continued

| Mole % | R¹ | R² | R³ |
|---|---|---|---|
| 1989 Compound V2B 0.7% | β-D-Xylose | H | [fatty acyl moiety structure] |

OBI-821 saponin can comprise an isolated compound of formula I where:
(i) R¹ is β-D-Apiose, R² is the fatty acyl moiety for the 1857 compound depicted above, and R³ is H (1857 compound V1LA);
(ii) R¹ is β-D-Apiose, R² is H, and R³ is the fatty acyl moiety for the 1857 compound depicted above (1857 compound V1B);
(iii) R¹ is β-D-Xylose, R² is the fatty acyl moiety for the 1857 compound depicted above, and R³ is H (1857 compound V2A); or
(iv) R¹ is β-D-Xylose, R² is H, and R³ is the fatty acyl moiety for the 1857 compound depicted above (1857 compound V2B). Collectively, 1857 compound V1A, 1857 compound V1B, 1857 compound V2A and 1857 compound V2B are called "1857 compounds mixture."

Table 10 summarizes the functional groups of 1857 compounds and the mole % of each 1857 compound in the 1857 compounds mixture. HPLC.

Table 10

TABLE 10

| Mole % | R¹ | R² | R³ |
|---|---|---|---|
| 1857 Compound V1A 64.7% | β-D-Apiose | [fatty acyl moiety structure] | H |

TABLE 10-continued

| Mole % | R¹ | R² | R³ |
|---|---|---|---|
| 1857 Compound V1B 1.3% | β-D-Apiose | H | |
| 1857 Compound V2A 33.4% | β-D-Xylose | | H |
| 1857 Compound V2B 0.6% | β-D-Xylose | H | |

OBI-821 saponin comprises one or more of the following compounds:
(i) 1857 compound V1A;
(ii) 1857 compound V1B;
(iii) 1857 compound V2A;
(iv) 1857 compound V2B;
(v) 1989 compound V1A;
(vi) 1989 compound V1B;
(vii) 1989 compound V2A; or
(viii) 1989 compound V2B.

In one embodiment, the Immunogenic agent can include OBI-822 and related variants.

In certain embodiments, the immune response can include: IgG (including subclasses IgG1, IgG2, IgG3, IgG4), IgM, CTLs (cytotoxic lymphocyte) directed to Globo H series antigens/tumor.

In certain embodiments, clinically meaningful benefits can include modulations in: Progression free survival; overall survival; (well tolerated and/or no major safety concerns); objective response rate; time to progression; disease free survival; tumor response; improvements in quality of life; reduction in size of solid tumors, and/or reduction in tumor associated antigens (primarily or including Globo H).

In certain aspects, administration regimen can include: Administer vaccine two or more times (e.g., 3, 4, 5, 6, 7, 8, 9, 10 or more times); adjusting time interval and/or dosing amount regimen between two successive administrations; adjusting routes of administration and/or altering/alternating injection sites/locations of administration or ANY combination of any of the above, whereby each administration increases the immune response [e.g. titer—IgG and/or IgM Ab amount, and/or increases affinity/avidity; induction of Abs to less immunogenic sites of Globo H portion of the Globo H antigen-conjugate (e.g., portions of Globo H antigen that may be less accessible in the conjugate)]. In certain aspects the injections can be altered and/or supplemented by the addition of immune response booster agents.

In certain aspects, modulation of Globo series antigens interaction can include: Induction of anti-Globo H antibodies with increased affinity with multiple rounds of vaccination; expansion of germinal centers of B cells to Globo H series tumor antigens; preferential expansion of germinal centers containing high affinity anti-Globo H antibodies; induction of low frequency B cells normally not present in sufficient numbers to produce meaningful responses with single (or low repetition of exposure to antigen) (e.g., they may bind to epitopes to which few antibodies bind); expansion of antibody secreting plasma cells ("antibody secreting plasma cells" are what B cells differentiate into) and memory B cells which may be important for long term maintenance of the anti-tumor response; increase kinetics of Ab class switching [need good T cell helper function or B cells will not switch to IgG]; increase in kinetics of antibody response (e.g., successive vaccination may lead to more rapid expansion of antibody than obtained without either conjugation to KLH, without co-administration of cyclophosphamide, and/or without repeated vaccinations; reduction of Treg activity that interferes with the development and maintenance of the above anti-tumor response; induction of Antibody-Dependent Cellular Cytotoxicity (ADCC) and Complement-Dependent Cytotoxicity (CDC) for tumor killing; induction of anti-Globo series antigens IgM/IgG immune response to elicit CDC and ADCC mediated tumor cell killing; induction of anti-Globo series antigens antibodies trap Globo series antigens-ceramide shedding from tumor cells to block translin-associated factor X (TRAX)-dependent angiogenesis; induction of anti-Globo series antigens antibodies to block Globo series antigens-ceramide induced Notch 1-dependent immunosuppression and thereby enhancing T cell proliferation and cytokine production; induction of anti-Globo series antigens antibodies to lead to apoptosis; Inhibition of Globo series antigens induced angiogenesis; OBI-822 vaccination induces apoptosis; Induction of CTLs (cytotoxic lymphocyte).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 illustrated the Negative Control (Patient No: 065) with ovarian cancer clinical trial of OBI-822 Treatment.

FIG. 11 illustrated the Stage III Ovarian Cancer (Patient No: 035) with ovarian cancer clinical trial of OBI-822 Treatment.

FIG. 12 illustrated the Stage IV Fallopian Tube Cancer (Patient No: 041) with ovarian cancer clinical trial of OBI-822 Treatment.

FIG. 13 illustrated the Stage III Ovarian Cancer (Patient No: 060) with ovarian cancer clinical trial of OBI-822 Treatment.

FIG. 14 illustrated the procedure of Investigational Drugs Mixing.

DETAILED DESCRIPTION OF THE INVENTION

Figure 1:
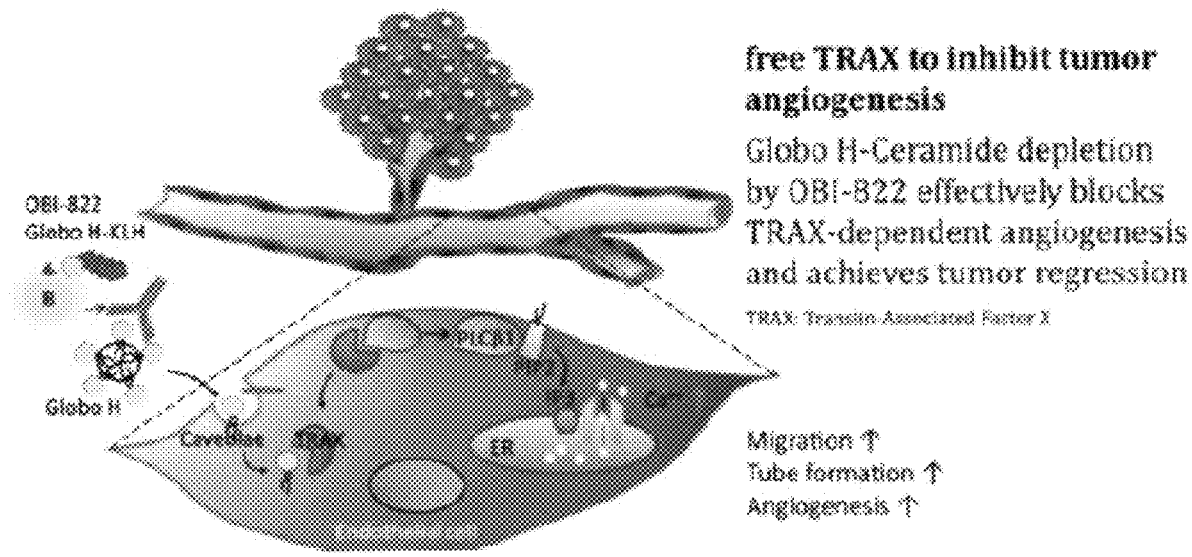
FIG. 1. OBI-822: Active cancer immunotherapy induces ADCC and CDC for tumor killing. Globo H-ceramide depletion by OBI-822 effectively blocks TRAX-dependent angiogenesis and achieves tumor regression. Tumor-secreted soluble factors bind to their respective receptors on endothelial cells, trigger phospholipase C (PLC) activation and intracellular calcium release, and promote proliferation, migration, and tube formation of endothelial cells. PLC serves as an "early generator" of second messengers, driving early stages of angiogenesis. PLC activity is regulated by several binding partners, including translin-associated factor X (TRAX), which blocks PLCβ1 activity. The molecular mechanism of this event involves the binding of Globo-H ceramide to TRAX with consequent release and activation of PLCβ1.
Figure 2:
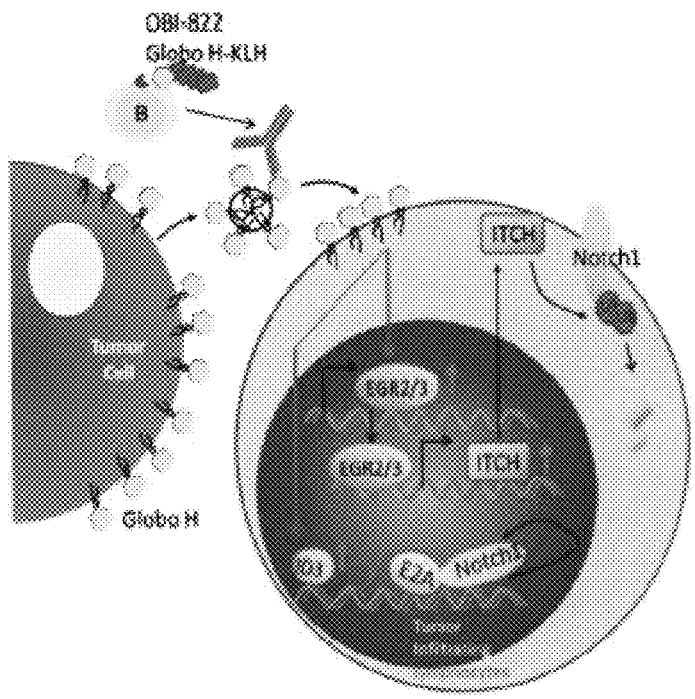
FIG. 2. OBI-822 depletes Globo H-ceramide, which in turns increases Notch 1 degradation, blocking the tumor immunosuppression effect, leading to tumor regression. The Notch signaling pathway is an evolutionarily conserved cell signaling system in most organisms, and it can regulate cell proliferation, differentiation, apoptosis, and survival. The regulation of Notch 1 is controlled by the E-protein transcription factor E2A and its natural inhibitor ID3. It is degraded by ubiquitination though E3 ubiquitin ligase, ITCH. Addition of Globo-H ceramide to immune cells could inhibit their proliferation and cytokine or immunoglobulin secretion. Globo-H ceramide could induce immunosuppression which involved inhibition of Notch 1 signaling through the induction of ID3 and EGR2/3 accompanied ITCH expression.
Figure 3:
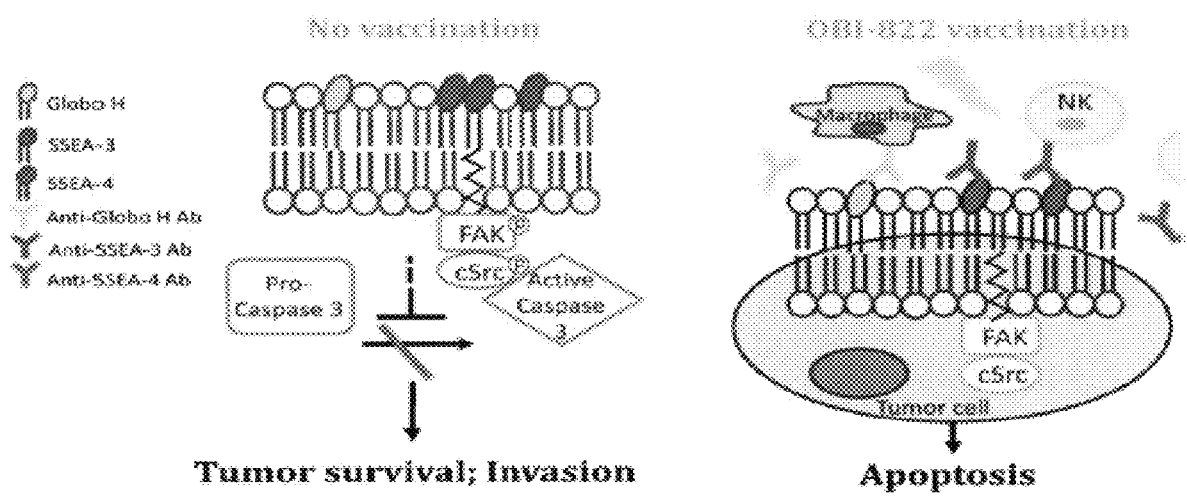
FIG. 3. OBI-822 leads to apoptosis. Apoptosis (programmed cell death) contributes to the normal development and tissue remodeling of multicellular organisms. Focal adhesion kinase (FAK) has been implicated in the integration of signals from integrins, oncogenes, and neuropeptides. Proteolytic cleavage of FAK by caspase-3 has been reported during growth factor deprivation-induced apoptosis in human umbilical vein endothelial cells, which implies an association between FAK and apoptosis.

The present invention relates to methods for immunotherapy of a subject afflicted with diseases such as cancer or an infectious disease, which methods comprise administering to the subject a composition comprising a therapeutically effective amount of a compound or agent that potentiates an endogenous immune response, either stimulating the activation of the endogenous response or inhibiting the suppression of the endogenous response. More specifically, this disclosure provides methods for potentiating an endogenous immune response in a subject afflicted with cancer so as to thereby treat the patient, which method comprises administering to the subject a therapeutically effective amount of an immunogenic agent.

Definitions:

"Administering" As used herein, embodiments of Administration regimen can include the following features: 1) Administer vaccine two or more times (e.g., 3, 4, 5, 6, 7, 8, 9, 10 or more times); 2) Each administration increases Immune Response (see above) [titer—IgG and/or IgM Ab amount, and/or increases affinity/avidity; induction of Abs to less immunogenic sites of Globo H portion of the Globo H antigen-conjugate (e.g., portions of Globo H antigen that may be less accessible in the conjugate)].

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

"Adverse Event" (AE) Toxicity will be measured according to US NCI Common Toxicity Criteria, Version 4, developed by the Cancer Therapy Evaluation Program at the National Cancer Institute. The criteria for unacceptable toxicities should include any≥Grade 4 toxicity, with the exception of local skin reactions, fever, chilling, sweats, urticaria, and/or pruritus since these are common side effects of antibody/adjuvant administration, are reversible, and controlled by supportive management. Theoretically, immune complex disease as manifested by skin, joint, renal, or other manifestations could occur, but these should be rare in the absence of prior exposure to mouse protein. These will be an indication to stop therapy in the affected subjects, but accrual of new subjects may continue. An adverse event is any physical or clinical change or disease experienced by the subject from the date of randomization and up to two years from randomization for subjects continuing in the follow up period, whether or not considered related to the use of the investigational drug. This includes the onset of new illness and the exacerbation of the preexisting condition. For subjects who withdraw treatment during the treatment period, adverse events should be recorded through 28 days after the last administration of study treatment (OBI-822/OBI-821 or Control).

"Antibody" (Ab), "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas. The terms "antibody" and "immunoglobulin" are used interchangeably in the broadest sense and include monoclonal antibodies (e.g., full length or intact monoclonal antibodies), polyclonal antibodies, monovalent, multivalent antibodies, multi specific antibodies (e.g., bispecific antibodies so long as they exhibit the desired biological activity) and may also include certain antibody fragments (as described in greater detail herein). An antibody can be chimeric, human, humanized and/or affinity matured.

"Variable" and "Complementarity Determining Regions" (CDRs)

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

As used herein, "isolated antibody" can include an "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The term "monoclonal antibody" (mAB) as used herein refers to an antibody obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

"human monoclonal antibody" (HuMAb): A "human monoclonal antibody" is a mAb which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

"humanized antibody": Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"chimeric antibody" The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"antigen-binding portion" 'or "antibody fragment": "Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen.

In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

The terms "cancer" and "cancerous" refer to or describe the physiological condition in mammals that is typically characterized by unregulated cell growth/proliferation. Examples of cancer include, but are NOT limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. "Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

"Immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

"Immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

"Immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"Subject" includes any human or nonhuman animal.

"Therapeutically effective amount" or "therapeutically effective dosage" of a drug or therapeutic agent, such as an Ab of the invention, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

"Immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

"Tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

Immunogenic agent and Antibodies generated of the present invention may be constituted in a composition, e.g., a pharmaceutical composition, containing one Ab or a combination of Abs, or an antigen-binding portion(s) thereof, and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

Preferred subjects include human patients in need of enhancement of an immune response. The immunotherapeutic methods disclosed herein are particularly suitable for treating human patients having a disorder that can be treated by potentiating an immune response. In certain embodiments, the methods are employed for treatment of subjects afflicted with a disease caused by an infectious agent. In preferred embodiments, the methods are employed for treatment of subjects afflicted with, or at risk of being afflicted with, a cancer.

"Cancer Immunotherapy"—As used herein, cancer immunotherapy can include, but not limited to, immune-based therapies capable of reducing tumor size in patients with metastatic cancer. Currently, there are three main approaches to cancer immunotherapy, a non-specific stimulation of immune reactions by stimulating effector cells and/or inhibiting regulatory cells, an active immunization to enhance specific anti-tumor reactions, known as cancer vaccines, and a passive transfer of anti-tumor antibodies or activated immune cells with antitumor activity, also known as adoptive immunotherapy (DeVita et al., 2008).

"Combination therapy" In certain embodiments, the immunomodulatory agents discussed herein may be used in combination with one or more anti-proliferative/chemotherapeutic agent that are effective for reducing tumor burden without significant systemic toxicity and may act to improve the effectiveness of the immune response. The agents can be combined as co-administration combination therapy and/or co-formulated combination therapy.

Combination therapy in which two or more drugs are used together in some dosing regimen or administration form, typically has one or more goals of: (i) reducing the frequency at which acquired resistance arises by combining drugs with minimal cross-resistance, (ii) lowering the doses of drugs with non-overlapping toxicity and similar therapeutic profile so as to achieve efficacy with fewer side effects, i.e., increase therapeutic index, (iii) sensitizing cells to the action of one drug through use of another drug, such as altering cell-cycle stage or growth properties, and (iv) achieving enhanced potency by exploiting additivity, or greater than additivity, effects in the biological activity of two drugs (Pegram, M., et al (1999) Oncogene 18:2241-2251; Konecny, G., et al (2001) Breast Cancer Res. and Treatment 67:223-233; Pegram, M., et al (2004) J. of the Nat. Cancer Inst. 96(10):739-749; Fitzgerald et al (2006) Nature Chem. Biol. 2(9):458-466; Borisy et al (2003) Proc. Natl. Acad. Sci. 100(13):7977-7982). Loewe additivity (Chou, T. C. and Talalay, P. (1977) J. Biol. Chem. 252:6438-6442; Chou, T. C. and Talalay, P. (1984) Adv. Enzyme Regul. 22:27-55; Berenbaum, M. C. (1989) Pharmacol. Rev. 41:93-141) and Bliss independence/synergy (Bliss, C. I. (1956) Bacteriol. Rev. 20:243-258; Greco et al (1995) Pharmacol. Rev. 47:331-385) are methods used for calculating the expected dose-response relationship for combination therapy compared to monotherapy based on parameters such as IC50, the dose of drug needed to achieve 50% target inhibition and equal to Ki in the simplest case.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v)

lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug-conjugate, gemtuzumab ozogamicin (MYLOTARG®, Wyeth).

Humanized monoclonal antibodies with therapeutic potential as chemotherapeutic agents in combination with the immunogenic/therapeutic agents of the present invention can include or exclude one or more of: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

"Standard-of-care therapeutic" is a treatment process, including a drug or combination of drugs, radiation therapy (RT), surgery or other medical intervention that is recognized by medical practitioners as appropriate, accepted, and/or widely used for a certain type of patient, disease or clinical circumstance. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2013).

Kits: Also within the scope of the present invention are kits, including pharmaceutical kits, for therapeutic uses, and diagnostic kits As used herein, additional aspects of the present disclosure includes aspects and factors relating to Dose escalation; patient Cohort; Safety; and Pharmacokinetics/Pharmacodynamics Analyses.

In broad terms, the immune system can be divided into innate and adaptive immunity. Innate immunity, is the more primitive of the two and is comprised of non-specific defenses, such physical barriers (e.g., the skin), non-specific defensive cells (e.g., macrophages) and variety of cytokines (e.g., IL-1). In general, vaccines will not upregulate innate system to a specific pathogen or disease, but adjuvants added to the vaccines may non-specific activate the innate immunity, which in turn may improve the adaptive-immune response. Adaptive immune can be further divided into humor (i.e., antibody) and cellular (e.g, cytotoxic T cells) immune responses. The effector cells of the humor immune response are comprised of cells that specialized solely in adaptive immunity (e.g., T and B lymphocytes); however, cells of innate immunity provide essential functions (e.g., antigen presentation). Thus, for example, the induction of antibody production to a virus would require a series of complex interactions of several cell types. Simplified, these would include capture and processing of viral components (e.g., virus' envelope proteins) by dendritic cells, which would in turn be presented to T cells specific to the presented antigen. Once activated by presented antigen, the T cells would "help" virus-specific B cells to generate antibodies to the invading pathogen.

Tolerance

It has long been recognized that while the immune system has the capability to recognize host antigens, normally, such responses are not observed (i.e., the immune system exhibits tolerance to self). This tolerance to self includes both "normal" as well as tumor antigens.

In one aspect, the current disclosure features a vaccine capable of disrupting the immune system's tolerance to the tumor antigen Globo H.

Types of Tolerance

Tolerance can result from either central and/or peripheral tolerance. Central tolerance prevents maturation of T and B lymphocytes which recognize self. Self-tolerance is not absolute, and some B cells producing anti-self antibodies may be found in normal individuals. However, because of a lack of anti-self T-cell help to self-antigens—an essential component of B cell activation—antibodies to self are rarely found. Peripheral tolerance is the ongoing active suppression of the immune response to self, and is thought to be primarily maintained by Treg cells. Treg's are thought to prevent the induction of T cell help to self antigens, which include both normal and tumor antigens.

Strategy to Break Tolerance to Self

In one aspect, the current disclosure features compositions and methods to overcome both central and peripheral tolerance to Globo H series tumor antigens. For example, in some aspects, the compositions and methods are useful in reducing Treg suppression and stimulating T-cell help to B cells producing anti-Globo H antibodies.

In some aspects, the current disclosure features co-administration of a Treg downmodulating agent to overcome peripheral tolerance. In aspects the Treg downmodulating agent may be cyclophosphamide, anti-Treg antibody or other agent that [selectively] inhibits Treg activity (more than other cells of the adaptive immune system).

Thus, in some aspects, cyclophosphamide can be administered to the patient concomitantly with the Globo H-KLH conjugate, thereby inhibiting Treg suppression of anti-Globo H antibody production. In some aspects, the Treg downregulating agent may also stimulate expansion of cytotoxic T lymphocytes to Globo H antigen positive cells, allowing the direct killing of Globo-H expressing tumor cells.

It is recognized that B cell antibody production requires help from a T cell that recognizes the antigen. However, central tolerance and/or antigen presenting deficiencies may result in a lack of T cell recognition of the Globo H (self) antigen. Accordingly, in some embodiments, this disclosure features compositions and methods for stimulating T-cell help to B cells producing anti-Globo H antibodies through conjugation of a Globo H series antigen to a strongly immunogenic agent, such as KLH. KLH is a phylogenetically distant organism and has a large molecular weight (over 390,000), both attributes known to increase immunogenicity. When the Globo H conjugate is administered to a patient, dendritic cells and/or other antigen-presenting cells process the Globo H conjugate, for example, the Globo H-KLH conjugate into Globo H and KLH components. T cells recognize the KLH antigen, which then helps B cells to produce the desired anti-Globo H antibodies.

Other Effects of Tumor Vaccines

Increased antibody titer: In some embodiments the compositions and methods of this invention features a clinical benefit by producing an antibody response above a threshold titer. Below the threshold titer, the antitumor response may be insufficient to produce a meaningful clinical benefit.

Increased affinity of anti-Globo H antibodies: In some embodiments the methods of this disclosure feature administering the Globo H conjugate to the patient two, three, four, five, six, seven, eight, nine, or ten or more times.

In some embodiments, repeated administration increases the affinity of the resulting antibody response as B cells expressing surface antibody with the highest affinity to Globo H are preferentially stimulated by injected antigen, because they bind the antigen better that B cells expressing lower affinity antibodies. In some embodiments, each cycle of administration increases the antibody response, increases the affinity and/or avidity of the antibodies, and/or induces production of antibodies to less immunogenic sites of the Globo H portion of the Globo H conjugate.

In some embodiments, repeated administration further induces low frequency B cells normally not present in sufficient numbers to produce meaningful responses with single (or low repetition of exposure to antigen) (e.g., they may bind to epitopes to which few antibodies bind), expansion of antibody secreting plasma cells ("antibody secreting plasma cells" are what B cells differentiate into) and memory B cells which may be important for long term maintenance of the anti-tumor response, and increase kinetics of Ab class switching.

In some embodiments repeated administrations also results in expansion of germinal centers of B cells to Globo H series tumor antigens and preferential expansion of germinal centers containing high affinity anti-Globo H antibodies Expansion of IgG subclasses: T cell help is able to induce B cells to switch their expression of heavy chain class and sub-classes. In humans, there are four IgG subclasses—IgG1, IgG2, IgG3 and IgG4. Each IgG subclass has biological effector function that differentiates it from the other subclasses. The expression of all four subclasses may maximize the tumor killing activity of the anti-Globo H response.

Increased kinetics in antibody response: In some embodiments, repeated inoculations of the Globo H-KLH conjugate, cyclophosphamide and adjuvant result in a more rapid expansion of antibody than obtained without conjugation to KLH, cyclophosphamide or repeated injections with adjuvant.

In certain embodiments, OBI-822 can block cancer immunosuppression by reducing Globo-H induced Notch signaling.

In certain aspects, OBI-822 can counteract certain negative traits of Globo-H in cancer treatment.

In certain embodiments, OBI-822 depletes Globo H, which in turns increases Notch 1 degradation, blocking the tumor immunosuppression effect, leading to tumor regression.

In certain embodiments, OBI-822 can counteract Globo-H associated reduction of T cell proliferation and cytokine secretion.

In certain embodiments, OBI-822 can counteract Globo-H associated inhibition of B cell differentiation and Ig secretion.

The roles of Globo Series antigens in cancer development is important. In certain embodiments, they can influence tumor survival by inhibiting the caspase 3 activation. In certain embodiments, revert caspase 3 inactivation, leading to apoptosis.

In certain embodiments, Globo-series clustering enhances tumor survival by inhibiting the caspase 3 cascade.

EXAMPLES

Until Applicants' present disclosure and exemplary data in support of affirmative immunogenic response and therapeutic efficacy, there is no prior conclusive demonstration/report of the effective use of the immunomodulatory agents as disclosed herein related to successful use of OBI-821 as an Adjuvant as evidenced in the examples section, including Pre-clinical Studies of Globo H Vaccine; OBI-822 with QS-21 in Phase I trials; and OBI-822 with OBI-821 in Cancer Clinical Trials.

Trial Overview: Globo H is a glycolipid found to be highly expressed in breast cancer. Active immunotherapy with OBI-822, a Globo H-KLH conjugate, and OBI-821, an adjuvant in two Phase I trials, induced Globo H specific antibodies which can mediate in vitro binding and cytotoxicity to Globo H expressing breast cancer cells.

Methods: In the international, randomized, double-blind, and placebo-controlled Phase II/III trial (NCT01516307), patients with metastatic breast cancer who had ≤2 events of progressive disease (PD), and who achieved at least stable disease (SD) after ≥1 anticancer regimen are randomized 2:1 to receive subcutaneous OBI-822 (30 µg Globo H)/OBI-821 (100 µg) or control (PBS), in combination with low-dose cyclophosphamide (300 mg/m$^2$) on Weeks 1, 2, 3, 5, 9, 13, 17, 25, 37, or until PD. Hormone therapy is allowed. The primary and secondary efficacy end points are progression-free survival (PFS) and overall survival (OS), correlated with humoral antibody response.

Results: 349 patients were randomized, 348 received study drug (ITT), 168 (48%) received all 9 injections. 70% had hormone receptor positive breast cancer, 13% were triple negative, and 62% received hormone therapy. No difference was observed in PFS (HR, 0.96 [95% CI, 0.74-1.25] P=0.77) or in interim OS (HR, 0.79 [95% CI, 0.51-1.22] P=0.29) across all patients, including patients who developed a Globo H specific IgG response, and those that did not develop a Globo H specific IgG response. However, PFS and OS were significantly improved in the 50% of patients who developed a Globo H specific IgG response to OBI-822/OBI-821 with a titer≥1:160 at any time during treatment vs. control (HR, 0.71 [95% CI, 0.52-0.97] P=0.029 for PFS; HR, 0.57 [95% CI, 0.33-0.97] P=0.04 for OS) and vs non-responders (HR, 0.52 [95% CI, 0.37-0.71] P<0.0001 for PFS; HR, 0.52 [95% CI, 0.29-0.92] P=0.025 for OS), adjusted for baseline disease status and/or hormone use. In a time-dependent Cox model, PFS was improved in patients who received all 9 injections of OBI vs control (HR, 0.66 [95% CI, 0.42-1.01] P=0.057). OBI-822/OBI-821 was well tolerated; the most common drug-related adverse event was grade 1/2 injection reaction.

Conclusion: Vaccination with OBI-822/OBI-821 did not improve PFS in the ITT. However, PFS and interim OS were significantly improved in patients who developed an immune response to the vaccine. These sub-group data are used to design a definitive Phase III trial.

Rationale for Trial Design: OBI-822 is a new, investigational anti-cancer treatment that belongs to a novel class of active immunotherapies. It is a synthetic glycoprotein comprised of a tumor-associated carbohydrate antigen (TACA), Globo H, covalent bounded to a carrier protein, Keyhole Limpet Hemocyanin (KLH). OBI-821 is a saponin-based adjuvant. Globo H is expressed in high levels on the surface of malignant tumors in many epithelial cancers, such as breast, prostate, gastric, lung, colon, pancreatic, and ovarian cancer, etc. The immunogenicity of the antigen is enhanced by conjugating Globo H to the KLH carrier protein to form OBI-822 (Globo H-KLH), and co-administered with an adjuvant, OBI-821.

Study Design: The international, randomized, double-blind, and placebo-controlled Phase II/III trial (NCT01516307) consists of 9 injections of OBI-822 in a 41-week treatment period, a disease progression follow-up period of up to 2 years from randomization, and a survival follow-up period of up to 5 years. A total of 349 previously treated women with histologically or cytologically confirmed metastatic BC are randomly assigned (2:1) to treatment with subcutaneous OBI-822 (30 μg Globo H)/OBI-821 (100 μg) or control (PBS), in combination with low-dose cyclophosphamide (300 mg/m$^2$).

Eligibility Criteria: (Inclusion and Exclusion Criteria were Established)
1. Inclusion Criteria
2. Exclusion Criteria Study Procedure Schedule:
1. Screening Phase—3 weeks prior to Randomization (Visit 1)
2. Treatment Period: Week 1—Week 3 (Visit 2—Visit 5)
3. Treatment Period: Week 5—Week 41 (Visit 6—Visit 19)
4. Follow-up Period (Every 8 weeks)
5. Early Termination criteria was established
6. Survival Follow Up Period (Every 12 weeks)
7. Other study procedure were considered for completeness Treatment Plan: (Items Considered)
1. Randomization and Blinding
2. Cyclophosphamide Administration Schedule
3. OBI-822/OBI-821 and Placebo Administration Schedule Management of Toxicity and Treatment Discontinuation: (Exemplary Factors that were Considered as Part of the Design)
1. General Management
2. Management of Drug-Induced Toxicities
3. Guidelines for Individual Subject Study Treatment (OBI-822/OBI-821, Placebo) Discontinuation
4. Guidelines for Cyclophosphamide Treatment Discontinuation Treatments Permitted and Prohibited During Study: (Exemplary Factors Considered as Part of the Design)
1. Permitted treatments during study
2. Prohibited treatments during study Drug Information: (Exemplary Factors Considered as Part of the Design)
1. Cyclophosphamide
2. OBI-822 (Globo H-KLH)
3. OBI-821
4. Clinical Trial Material (CTM) Supply, Packaging, Labeling, and Storage Study Endpoint:
1. Efficacy Assessment
2. Safety Assessment
3. Safety Variables Response Criteria:
1. Definitions for Measurability of Tumor Lesions
2. Recording Tumor Lesions
3. Response Evaluation
4. Criteria for Removal from Protocol Therapy
5. Off Study Criteria Statistical Consideration:
1. Objectives and Hypotheses
2. Target Sample Size
3. Evaluation of Study Endpoint
4. Statistical Methods
5. Safety Analysis Adverse Event:
1. Definition of Adverse Event:
2. Assessment of Relationship to Treatment Demonstration of efficacy: In certain embodiments, OBI-822/OBI-821 with cyclophosphamide improved the "Responders" (with increasing Globo H specific IgG/IgM) compared to "Non-Responders" (with no IgG/IgM response) with Metastatic breast cancer.

Frequency and magnitude of humoral immune responses (Globo H specific IgG/IgM) after immunization and their correlation with PFS and OS in patients with Metastatic breast cancer.

Safety and Toxicity profile of OBI-822/OBI-821 with cyclophosphamide relative to PBS with cyclophosphamide.

Clinical trial as a Specific Example: A Double-blind, Randomized Phase II/III trial of Active Immunotherapy with Globo H-KLH (OBI-822) and OBI-821 adjuvant in Subjects with metastatic breast cancer.

Treatment Plan: This is a double-blind, randomized, two-arm, Phase II/III trial in subjects with metastatic breast cancer.

Tumor Assessment at screening: Full body CT scans (chest, abdomen, and pelvis) are performed at screening and used as the baseline scan. If full-body CT scan has been performed within 2 weeks of the screening scan, then this performed scan can be used as the baseline scan. If full body CT scans prior to screening is not available, sections with lesions after diagnosis of metastatic breast cancer must have imaging from CT or Mill scan to confirm the tumor status.

Tumor response status (SD, PR, CR) is based on RECIST 1.1 criteria. Confirmatory CT scan at screening (baseline) was compared with previous full body CT scan prior to screening. The disease status of the scans previous to the screening scans must be the same disease status as the screening scans. An interval of at least 6 weeks is required for SD, and an interval of at least 4 weeks is required for PR and CR.

If a new lesion is detected at screening (i.e., tumor not evident on previous imaging and/or tumor not previously documented on imaging), the case is considered PD, and thus not eligible for inclusion.

Disease status for stratification is classified into either with evidence of disease (PR/SD) or without evidence of disease (CR).

For subjects with no evidence of disease (CR) due to excision of a metastatic lesion prior to screening, the investigator needs to ensure that the tumor response status is documented by imaging prior to surgical removal.

The tumor status is recorded as the evidence of disease (PR/SD) if enrolled.

Imaging is assessed by site radiologists and a copy is sent to central radiology laboratory for an independent review, which is not interfered with the sites' interpretation and decision.

Subjects are randomized to receive either OBI-822/OBI-821 (Treatment Group) or PBS (Control Group) in a 2:1 allocation.

Subjects are stratified according to their usage of hormone therapy while on study and their disease status at entry.

When enrolled as a hormone therapy non-user, patients are not allowed to start hormone therapy while on study.

If enrolled as a hormone therapy user, patient should be on hormone therapy.

Change to another regimen of hormone therapy due to intolerance of toxicity from previous hormone therapy is allowed.

There are four strata:
1. Hormone Therapy User—With Evidence of Disease (PR/SD)
2. Hormone Therapy User—Without Evidence of Disease (CR)
3. Hormone Therapy Non-User—With Evidence of Disease (PR/SD)
4. Hormone Therapy Non-User—Without Evidence on Disease (CR)

Collect subject tumor biopsy/tissue samples to test for tumor Globo H Expression and to correlate with treatment response.

In certain combination therapy embodiments, treatment subjects are given cyclophosphamide (300 mg/m$^2$) intravenously at Weeks 1, 5, 9, 13, 17, 25 and 37 (Visits 2, 6, 8, 10, 12, 14, and 17) or until disease progression.

OBI-822/OBI-821 or Control (PBS) is given subcutaneously on Weeks 1, 2, 3, 5, 9, 13, 17, 25, and 37 (Visits 3, 4, 5, 7, 9, 11, 13, 15, and 18). Subjects are followed until disease progression or up to 2 years from randomization.

Blood samples are collected for evaluation of immune responses to Globo H-KLH during the treatment and follow up period for up to 2 years from the start of treatment or up to disease progression.

Tumor Assessment During Study
1. Full body CT scans (chest, abdomen, and pelvis) are performed at every 8 weeks until end of study or until disease progression.
2. CT scans from each time point are compared against the baseline scan (at screening) and previous time points for Progression Free Survival (PFS) and tumor response status (PD, SD, PR, CR), based on the RECIST 1.1 criteria.

All surviving subjects are followed-up at 12-week intervals up to 5 years from randomization for Overall Survival (OS).

For subjects with PD, blood and urine samples are drawn at the time of progression or before the subjects are taken off from the study.

Example 1

Clinical Trial Data of Progression-Free Survival (PFS) For Modified Intent-to-Treat (Mitt) Population of OBI-822

The Kaplan-Meier plots progression-free survival (PFS) and overall survival (OS) for modified intent-to-treat (mITT) population of OBI-822 (original name OPT-822) indicated that there was a higher PFS and OS after patients completed 9 injections of OBI-822 compared with placebo.

Clinical Trial Data of Human Anti-Globo H IgG Titer Determination by ELISA

Reagent/Buffer Preparation

Coating antigen: 1 mg/mL Globo H-ceramide was dissolved in ethanol (OBI Pharma Inc.); Secondary antibody for human serum: Goat anti-human IgG-AP (Jackson Immunoresearch, Cat #109-055-008); 10×PBS, pH 7.4 (Gibco, Cat #70011-044); Tween-20 (Sigma-Aldrich, Cat #P2287); Substrate Solution: Alkaline Phosphatase Yellow (pNPP) Liquid Substrate (Sigma-Aldrich, Cat #P7998); Blocking Buffer (Sigma-Aldrich, Cat #B6429); PBST: 0.05% tween-20 in PBS; Stop Solution: Alkaline Phosphatase Stop Solution (Sigma-Aldrich, Cat #A5852).

Assay Procedure

Globo H-ceramide was diluted to 4 µg/mL in ethanol. 50 µL of diluted Globo H-ceramide solution was added into each well of a standard reaction plate. The plate with the reaction mixture was incubated at room temperature for overnight. The plate was decanted and washed with PBST at 200 µL/per well for three times. 100 µL of Blocking Buffer was added to each well and incubated at room temperature for 30 minutes. The plate was decanted and washed with PBST 200 µL/well for three times.

Serum sample dilution: samples were two-fold serial diluted in Blocking Buffer ranging from 20, 40, 80, 160, 320, 640, 1280 to 2560 folds (40 µL of serum sample was added to 760 µL Blocking Buffer to make 20 fold dilution). 50 µL of serum sample was added into each well in coated and un-coated plates, and incubated at room temperature for 60 minutes. The plates were decanted and washed with PBST 200 μL/well for three times. 40 μL of 0.3 mg/mL stock anti-human IgG-AP secondary antibody was added to 7960 μL of Blocking Buffer for 1:200 dilution. 50 μL of the diluted anti-human IgG-AP was added into each well in coated and un-coated plates, and incubated at room temperature for 45 minutes. The plates were decanted and washed with PBST 200 μL/well for three times. 100 μL of Substrate Solution was added into each well of coated and un-coated plates, and incubated at 37° C. for 20 minutes. 50 μL of Stop Solution was added to each well. The plates were read at optical density 405 nm by ELISA reader.

Data Analysis

The cut-off value was obtained by the difference of mean OD value of secondary antibody only from coated plate and mean OD value of secondary Ab only from un-coated plate plus 0.1.

Titer was defined as the difference of the OD value of coated plate and OD value of un-coated plate at each dilution. The highest dilution above the cut-off value was the anti-Globo H IgG titer. Statistical analysis was performed using GraphPad Prism 6 software.

The characteristics of the clinical patients were listed in Table 1.

TABLE 1

The baseline Characteristic

| Characteristic | OPT-822/821 N = 224 | Placebo N = 124 | P-value |
|---|---|---|---|
| Age, years | | | 0.4826 |
| Median (range) | 53 (30-87) | 52 (30-82) | |
| Ethnicity n (%) | | | 0.4065 |
| Asian | 185 (82.6%) | 97 (78.2%) | |
| Caucasian | 39 (17.4%) | 27 (21.8%) | |
| ECOG Performance Status, n (%) | | | 0.9671 |
| 0 | 165 (74.0%) | 92 (74.2%) | |
| 1 | 58 (26.0%) | 32 (25.8%) | |
| Stage at initial diagnosis, n (%) | | | 0.7292 |
| Stage I-III | 141 (63%) | 80 (64.6%) | |
| Stage IV | 72 (32.1%) | 37 (29.8%) | |
| Unknown | 11 (4.9%) | 7 (5.6%) | |
| Time from first diagnosis to Day 1, months | | | 0.9786 |
| Median (range) | 50 (3-307) | 41 (5-390) | |
| Time from first metastatic diagnosis to Day 1, months | | | 0.5246 |
| Median (range) | 12 (1-87) | 14 (3-151) | |
| Number of Progression After Metastatic Diagnosis, n (%) | | | 0.8260 |
| 0 | 137 (61.2%) | 77 (62.1%) | |
| 1 | 67 (29.9%) | 37 (29.8%) | |
| 2 | 20 (8.9%) | 10 (8.1%) | |
| Biologic subtypes, n (%) | | | 0.7078 |
| ER(+) and/or PR(+), HER2(−) | 161 (71.9%) | 84 (67.8%) | |
| Triple negative | 28 (12.5%) | 17 (13.7%) | |
| HER2(+) | 35 (15.6%) | 23 (18.5%) | |
| Use of hormone therapy during the study, n (%) | | | |
| Yes | 140 (62.5%) | 76 (61.3%) | |
| No | 84 (37.5%) | 48 (38.7%) | |
| GLOBO H Expression, IHC, n (%) | | | 0.8704 |
| 0 | 44 (27.7%) | 25 (29.8%) | |
| 1+ | 57 (35.8%) | 30 (35.7%) | |
| 2+ | 27 (17.0%) | 10 (11.9%) | |
| 3+ | 31 (19.5%) | 19 (22.6%) | |
| Any expression | 115 (51.3%) | 59 (47.6%) | |

The progression-free survival (PFS) indicated that OBI-822 was reactive in several biological sub-type of breast cancer (Stage I, II, III, ER(+), PR(+), HER2(+) or triple negative). The profiles of Globo H expressions between different tumor subtypes were listed in Table 2.

TABLE 2

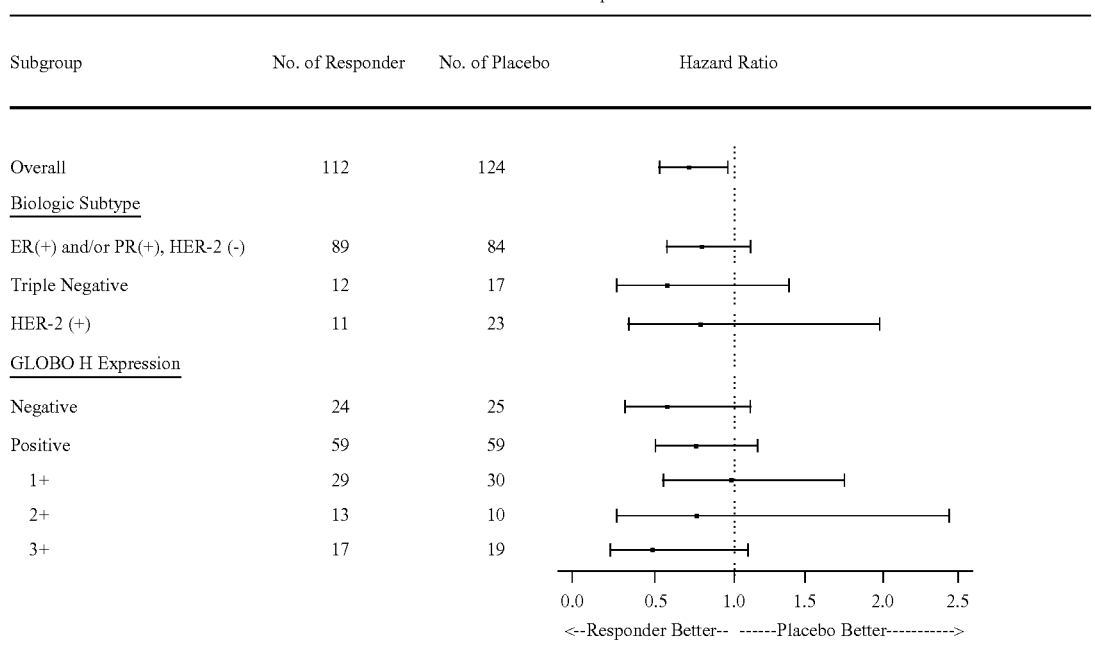

TABLE 2-continued

| PFS OBI-822/821 Immune Responder vs OBI-822/821 Non-Responder | | | |
|---|---|---|---|
| Subgroup | No. of Responder | No. of Non-Responder | Hazard Ratio |
| Overall | 112 | 112 | |
| Biologic Subtype | | | |
| ER(+) and/or PR(+), HER-2 (-) | 89 | 72 | |
| Triple Negative | 12 | 16 | |
| HER-2 (+) | 11 | 24 | |
| GLOBO H Expression | | | |
| Negative | 24 | 20 | |
| Positive | 59 | 56 | |
| 1+ | 29 | 28 | |
| 2+ | 13 | 14 | |
| 3+ | 17 | 14 | |

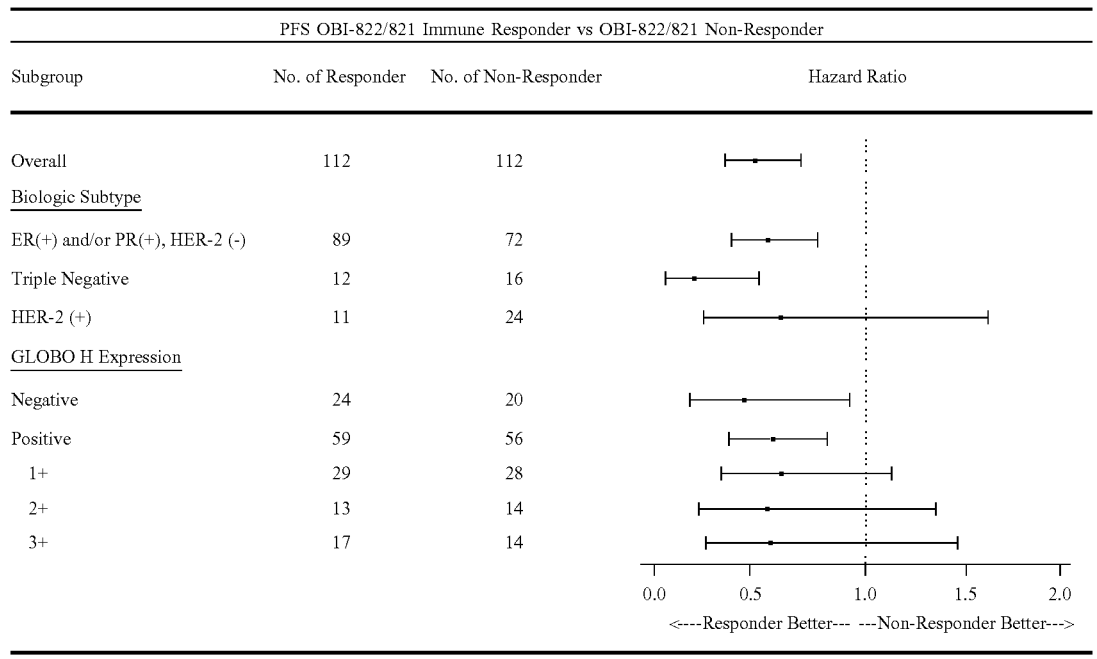

<---Responder Better--- ---Non-Responder Better--->

Figure 4:
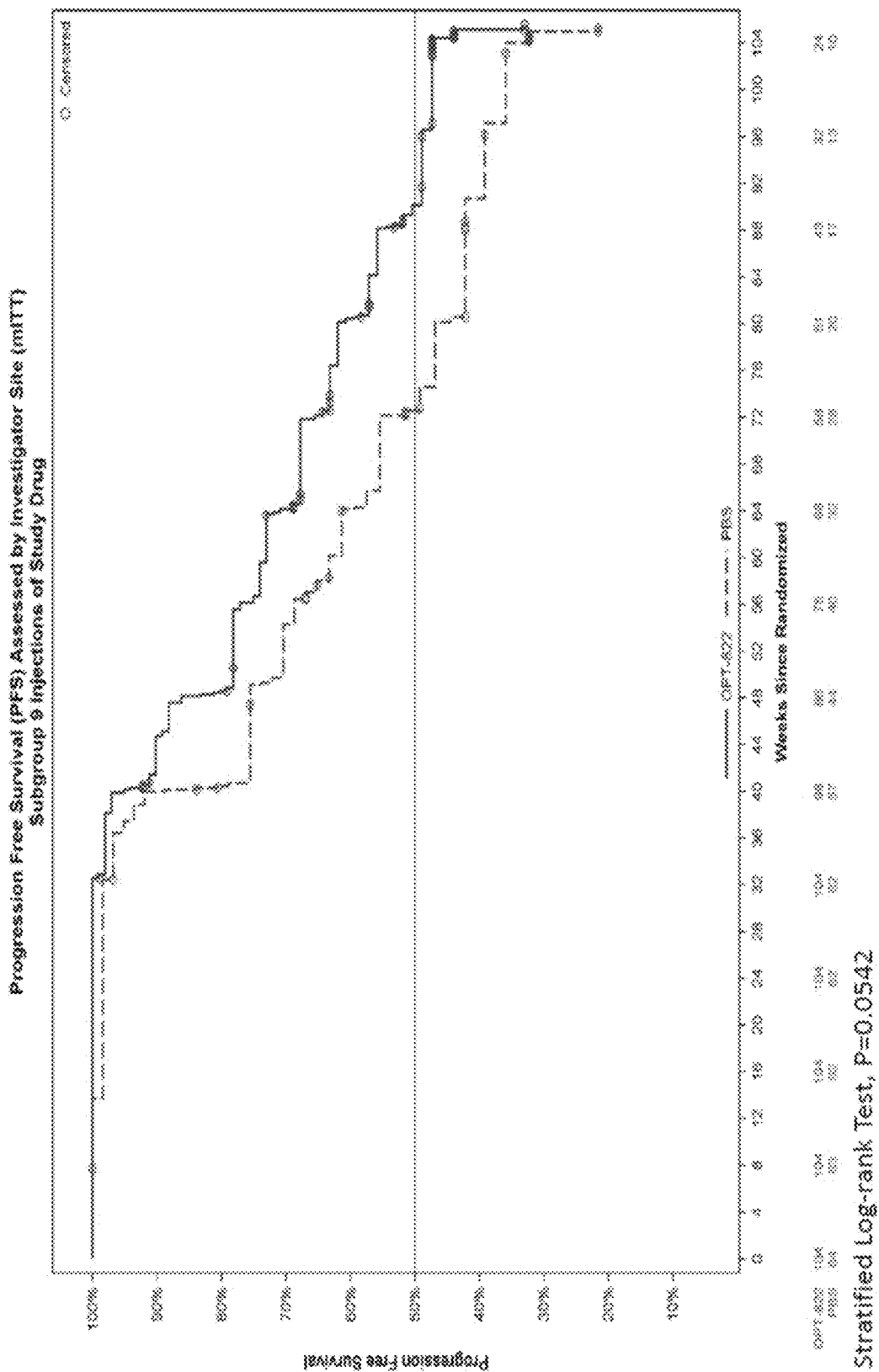
FIG. 4 illustrated the Progression-Free Survival (mITT) after received 9 Injections of Study Drugs (Stratified Log-rank Test, p=0.0542).
Figure 5:
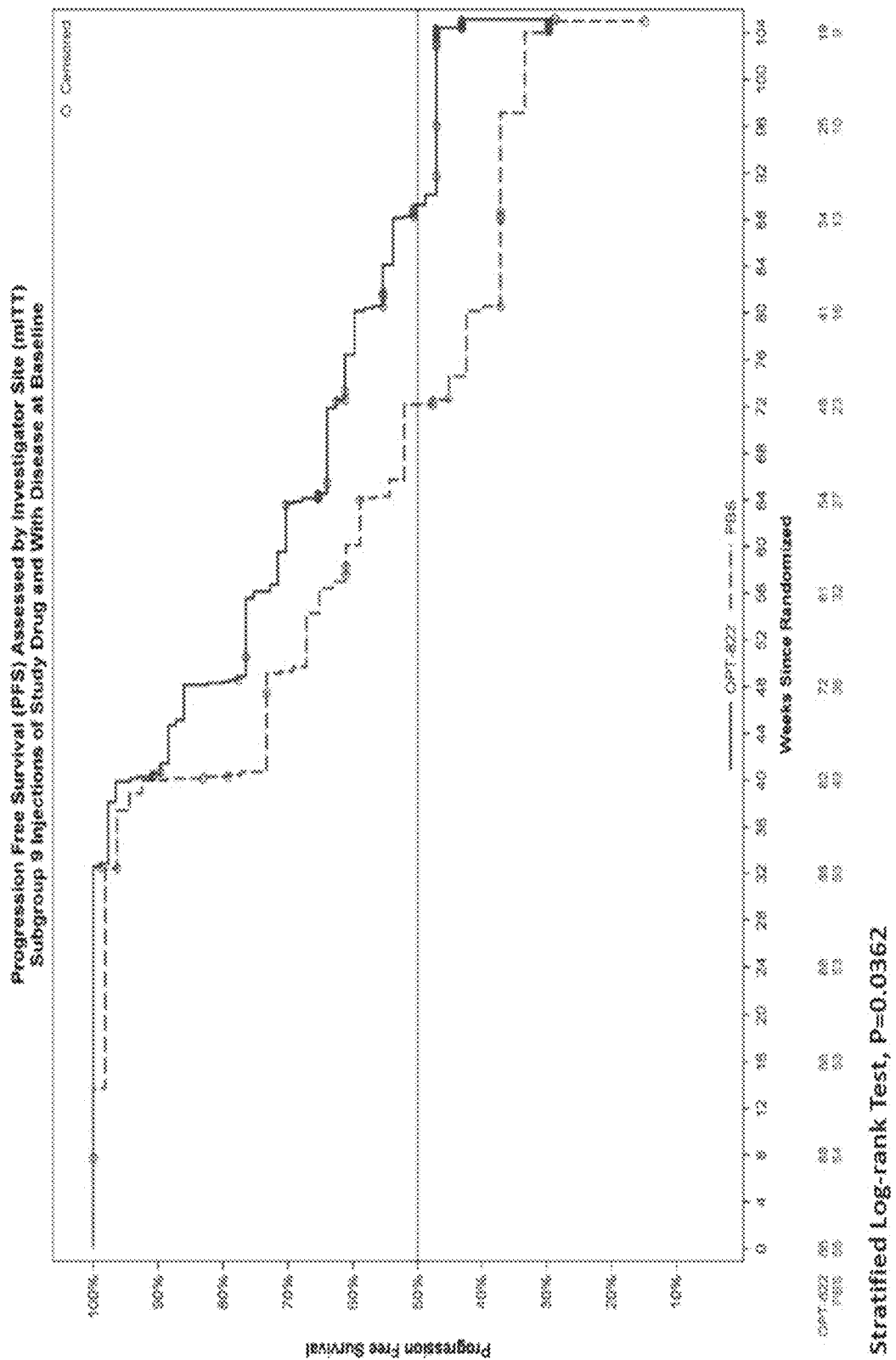
FIG. 5 illustrated the Progression-Free Survival (mITT) after received 9 Injections of Study Drugs and with Disease at Baseline (Stratified Log-rank Test, P=0.0362).

FIGS. 4 and 5 showed the Progression Free Survival (PFS) after received 9 injections of Study Drugs. It indicated that OBI-822 vaccine could extend the survival rate of breast cancer patients with a longer time.

Figure 6:
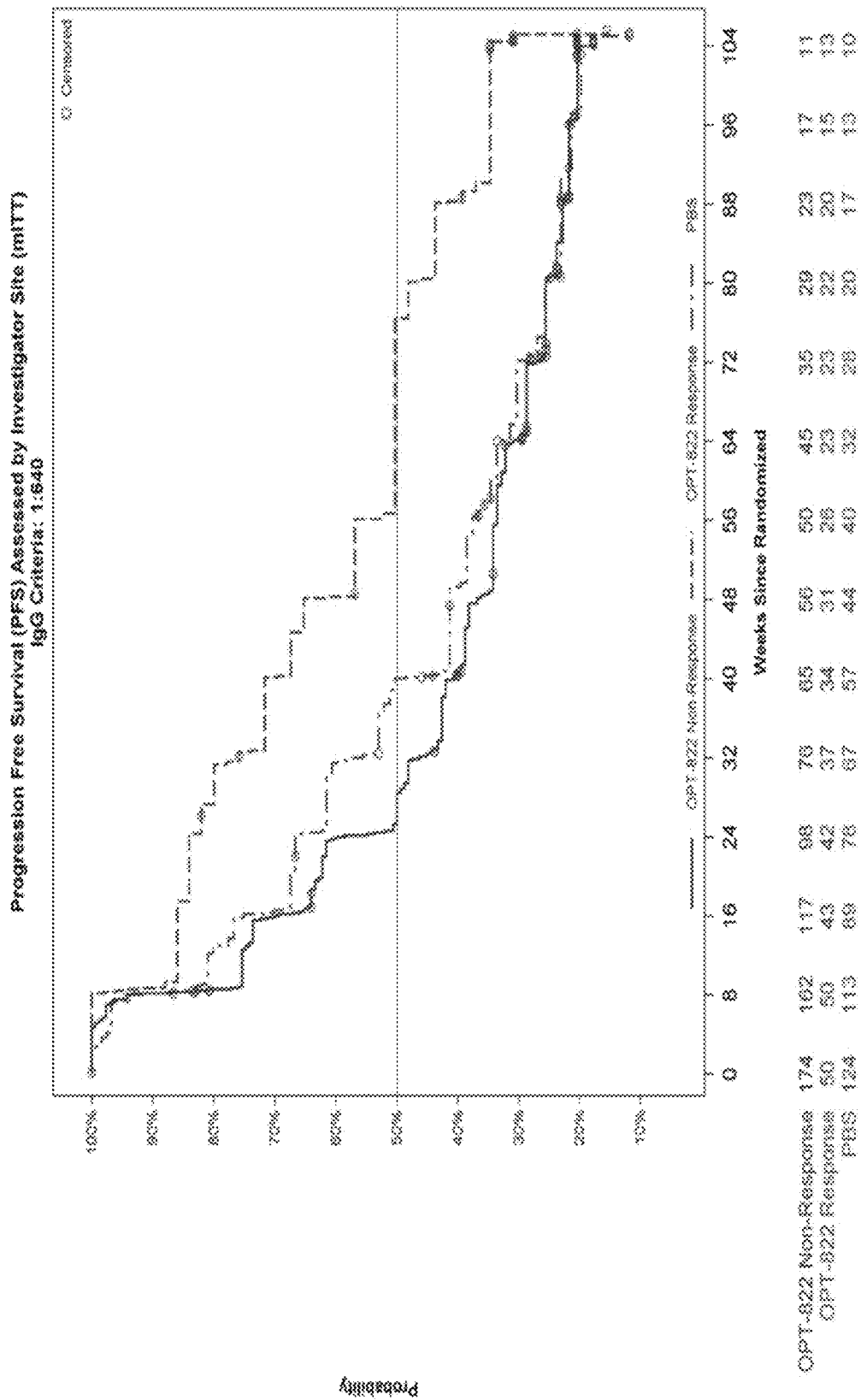
FIG. 6 illustrated the Progression-Free Survival (mITT) of Study Drugs Treatment with/without IgG immune response (IgG Criteria 1:640) vs placebo.
Figure 7:
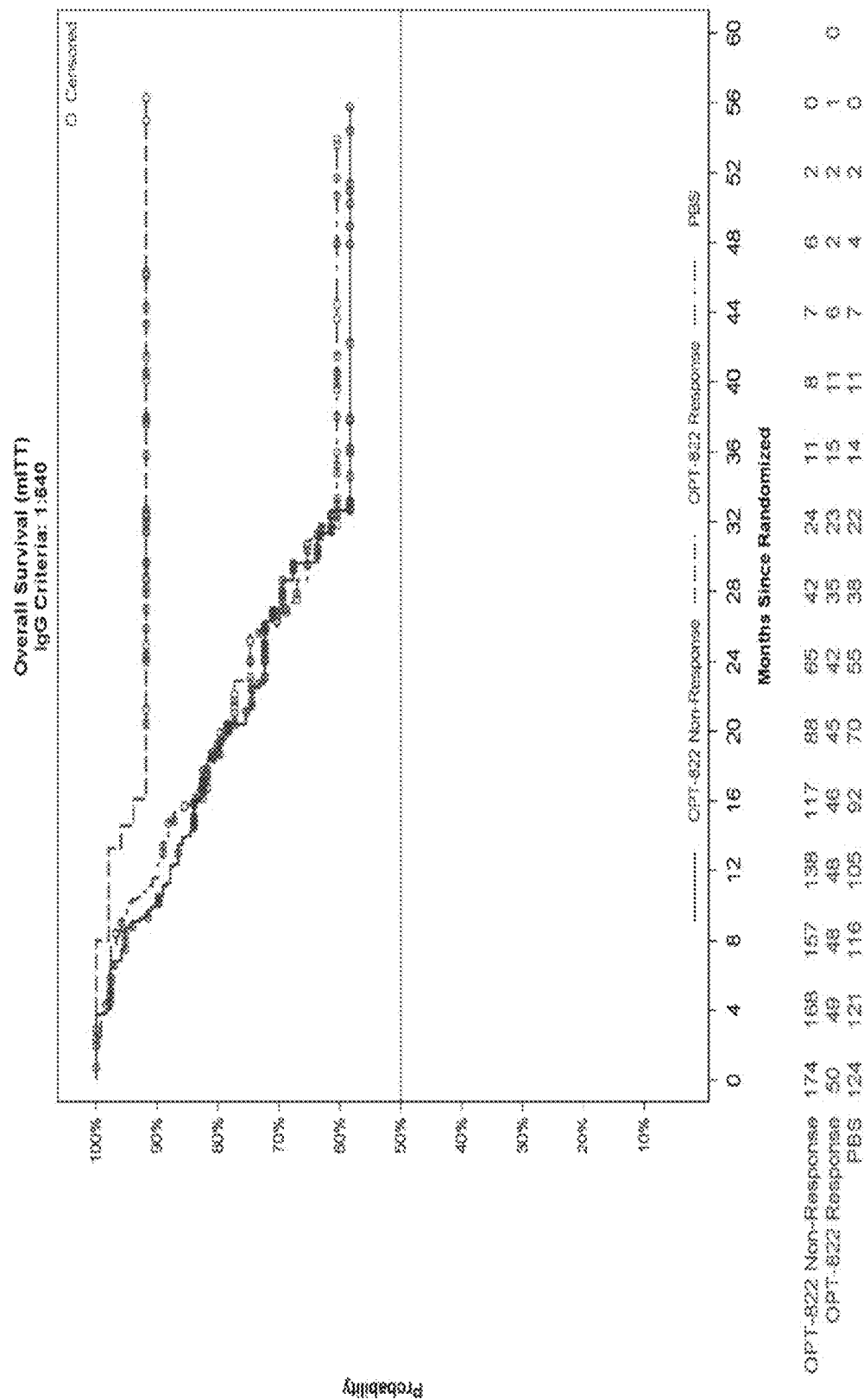
FIG. 7 illustrated the Overall Survival (mITT) of Study Drugs Treatment with/without IgG immune response (IgG Criteria 1:640) vs placebo.

FIGS. 6 and 7 showed the Progression Free Survival (PFS)/Overall Survival (OS) after received of Study Drugs with/without IgG immune response (IgG Criteria 1:640). It indicated that OBI-822 vaccine could induce IgG immune response and extend the survival rate of breast cancer patients with a longer time.

Clinical trial data of human Anti-Globo H IgM titer determination by Glycan Array Background Glycan Array platform utilizes automated Agnitio BioIC system in which ELISA is performed within the microfluidic cartridge. The microfluidic cartridge contains an array of microfluidic pumps and valves, a channel network, reagent storage reservoirs, a glycan array reaction zone, and a waste storage reservoir. Automated Agnitio BioIC system pumps reagents and samples from their respected reservoirs into a reaction zone for multiplexed ELISA reaction with chemical luminescence. The collected data are analyzed by the LabIT software provided by Agnitio Science and Technology Inc. The specification of equipment of Agnitio BioIC system was disclosed in a previous PCT patent application (WO2017041027A1).

Reagent/Buffer Preparation

Sixty-six microliter of Normal Human Serum (NHS) or serum from 220 breast cancer patient samples and 124 placebo samples were added in 594 μL Sample Diluent Buffer (BioCheck Inc., Cat #MB10175) to form ten-fold dilution. The Secondary Antibody Solution was prepared by mixing 2 μL Horseradish peroxidase (HRP)-conjugated goat anti-human IgM (KPL Inc., Cat #474-1003) in 98 μL Conjugate Buffer (SuperBlock (TBS) Blocking Buffer plus 0.2% Tween 20, Thermo Fisher Scientific Inc., Cat #37535) to form 50-fold dilution. 40 μL of diluted secondary antibody solution was pumped into 2360 μL Conjugate Buffer to form the Secondary Antibody Solution (3000× diluted).

Assay Procedure

Six hundred and twenty microliter Wash Buffer (Phosphate-buffered saline (Thermo Fisher Scientific Inc., Cat #70011) in 0.2% (v/v) Tween 20 (J. T. Baker, Cat #JTB-X251-07)) was added to the "Wash" reservoir. 120 μL Blocking Buffer (Protein-Free Blocking Buffers, Thermo Fisher Scientific Inc., Cat #37571) was added to the "Blocking" reservoir. 120 μL Secondary Antibody Solution was added to the "Conjugate" reservoir. 100 μL serum was added to the "Serum" reservoir. 120 μL Substrate Buffer (SuperSignal ELISA Femto Maximum Sensitivity Substrate, Thermo Fisher Scientific Inc., Cat #37074) was added to the "Substrate" reservoir in ten minutes.

Data Analysis

The glycan array was pressurized by Agnitio BioIC Pumping Machine for 30 minutes. The bound serum was visually monitored using Agnitio BioIC Analyzer. The absorbance intensity of array was converted into "Ab level (μg/mL)" relative to anti-human Globo H IgG. The internal curve was performed using 0.0625, 0.125, 0.25, 0.5, 0.75, and 1 μg/mL of human IgM. The linear regression of the internal curve of each chip was used to calculate the slope and the intercepts. In certain examples, the Ab level (μg/mL)=[(raw data-intercept)/slope]×0.1.

Figure 8:
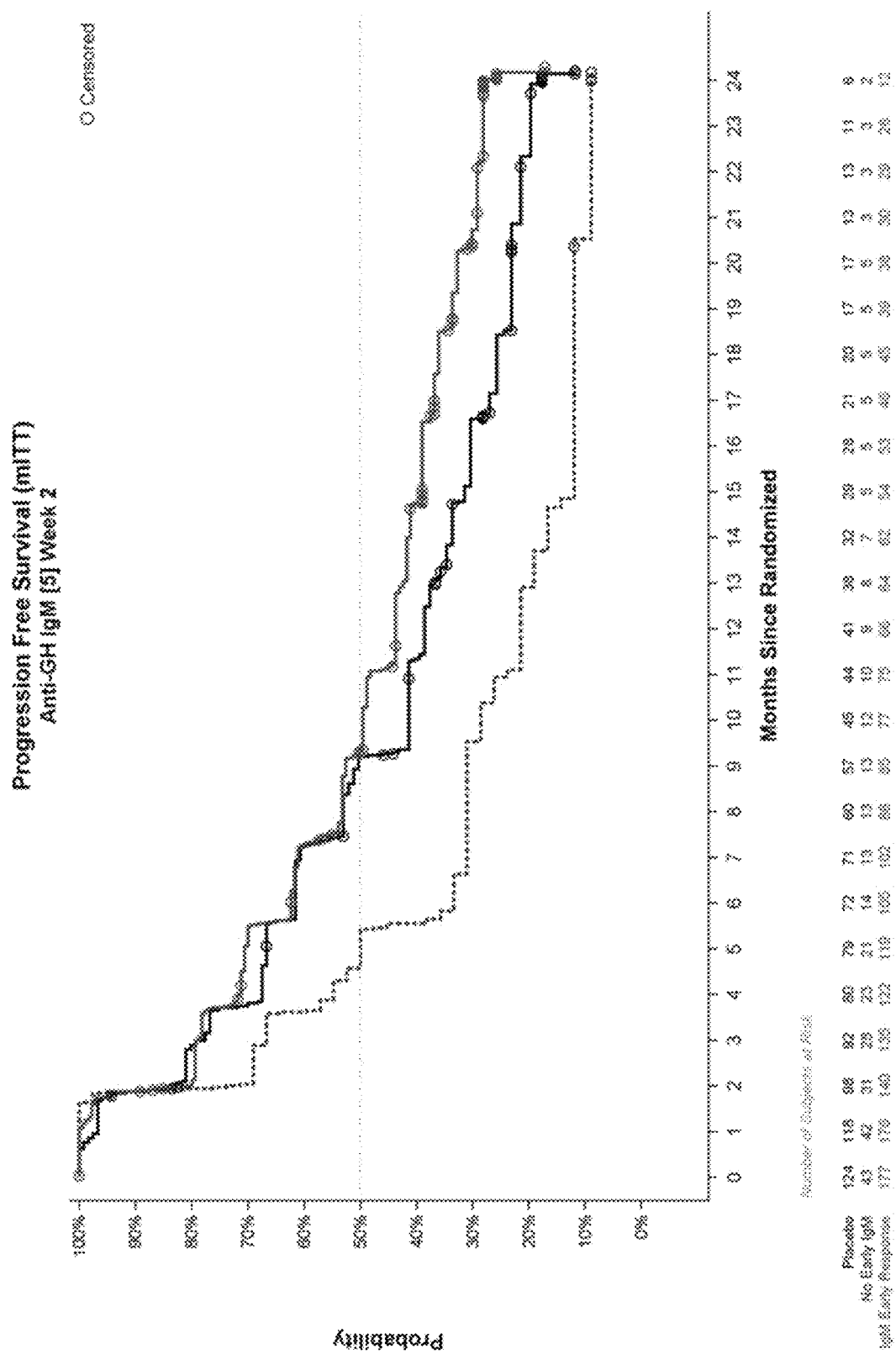
FIG. 8 illustrated the Progression-Free Survival (mITT) after received one injection of Study Drug on Week 2 with/without early IgM immune response (IgM Criteria) vs placebo.

FIG. 8 showed the Progression-Free Survival (PFS) after received one injection on Week 2 of Study Drug with/without early IgM immune response. It indicated that OBI-822 vaccine could induce early IgM immune response and extend the survival rate of breast cancer patients with a longer time.

Demonstration of Efficacy using Clinical trial data Based on Human Anti-Keyhole Limpet Hemocyanin (KLH) IgG Titer Assay Human Anti-Keyhole limpet hemocyanin (KLH) IgG titer assay was used to show that the immunological-reactions generated by the administration of Globo series antigens vaccine could be induced by the Globo series antigens vaccine, the Globo series antigen and/or the carrier protein.

Reagent/Buffer Preparation

KLH (Sigma-Aldrich, Cat #H1158, ocean harvest, stock concentration 5 mg/mL); Coating buffer: carbonate-bicarbonate buffer pH 9.2 (Sigma-Aldrich, Cat #C3041-50CAP); Secondary antibody: Goat anti-human IgG-HRP (KPL, Cat #474-1002); 10×PBS, pH 7.4 (Gibco, Cat #70011-044); Tween-20 (Sigma-Aldrich, Cat #P2287); TMB Substrate Solution (Clinical, Cat #01016-1-500); Blocking buffer (Sigma-Aldrich, Cat #B6429); PBST: 0.05% tween-20 in PBS; Stop solution: 1N $H_2SO_4$.

Assay Procedure

KLH was diluted to 4 µg/mL with coating buffer. Fifty microliter of diluted KLH solution was added into each well of a standard well. The plate was incubated at 4° C. overnight. The plates was decanted and washed with PBST at 200 µL/per well for three times. 100 µL blocking buffer was added to each well and incubate at room temperature for 30 minutes. The plate was decanted and washed with PBST 200 µL/per well for three times.

Serum sample dilution: samples were two-fold serial diluted with blocking buffer ranging from about 1000, 2000, 4000, 8000, 16000, 32000, 64000 to 128000 folds (1 µL of serum sample was added to 999 µL blocking buffer to make 1000 fold dilution). 50 µL of samples were added into each well in coated and un-coated plates, then incubated at room temperature for 1.5 hours. The plates were decanted and washed with PBST 200 µL/well for three times. Anti-human IgG-HRP secondary antibody was diluted to 1:20000 with blocking buffer. 1 µL was taken from 1 mg/mL stock and added to 20 mL of blocking buffer to make 1:20000 dilution. 50 µL of anti-human IgG-HRP was added into each well in coated and un-coated plates and incubated at room temperature for 45 minutes. The plates were decanted and washed with PBST 200 µL/well for three times. 100 µL of TMB substrate solution was added into each well of coated and un-coated plates, then incubated at room temperature for 5 minutes. 100 µL of stop solution was added to each well. The plate was read at optical density 450 nm by ELISA reader.

Figure 9:
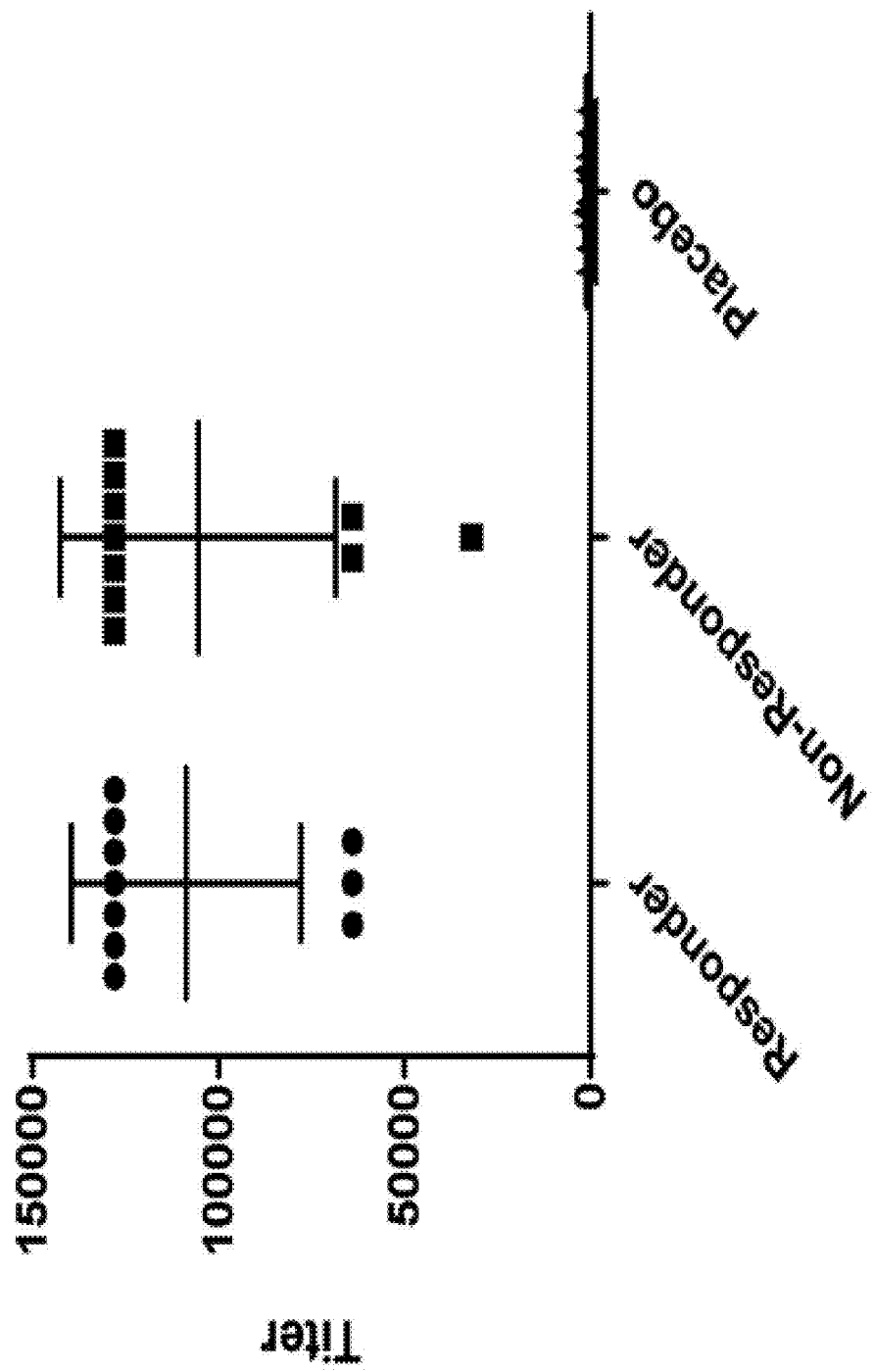
FIG. 9 showed there was a high anti-KLH IgG immune response after patients received the injections of OBI-822 vaccine.

FIG. 9 exhibited high anti-KLH IgG immune response after patients received the injections of OBI-822 vaccine. A total of 30 clinical serum samples were divided into three groups (Responder: Receiving OBI-822 vaccine injections with increasing anti-Globo H IgG/IgM level; Non-Responder: Receiving OBI-822 vaccine injections with no increasing anti-Globo H IgG/IgM level). It demonstrated that the administration of OBI-822 vaccine can indeed induce anti-KLH immune response. Therefore, the immunological-reactions generated by the administration of Globo series antigens vaccine can be induced by the Globo series antigens vaccine, the Globo series antigen or the carrier protein.

Example 2

Demonstration of Efficacy Using Representative Ovarian Cancer Model

Clinical trial as a Specific Example: An Open Labeled Phase II trial of Active Immunotherapy with Globo H-KLH (OBI-822/821) in Women Who Have Non-Progressive Epithelial Ovarian or Fallopian Tube Cancer.

Method: This was an open labeled, Phase II trial in women who had not progressed after having received cytoreductive surgery followed by platinum-based chemotherapy for newly diagnosed≥stage II epithelial ovarian or fallopian tube cancer.

For subjects who participate to receive the treatment, OBI-822 (30 mcg Globo H)/OBI-821 (100 mcg), were given subcutaneously on the Weeks 1, 2, 3, 4, 12, 20, 28, 36, 44, and 52 (Visits 1, 2, 3, 4, 5, 6, 7, 8, 9, and 10). Disease status was determined according to the results of evaluation incorporating RECIST 1.1 criteria. A subject was evaluated to have PD on the basis of objective RECIST 1.1 criteria. The CT Scan/MRI for RECIST criteria were performed at screening week 28 and 52. Whole abdominal (abdomen and pelvis) CT scan were performed at designated times during treatment with an interval of about 24 weeks. The window period for CT scan was +/−14 days from the planned visit per protocol schedule. Unscheduled tumor assessment was performed under investigator's discretion and at the time of assessment was consistent with the examination performed at baseline. For subjects that were CT-contraindicated, MRI was performed instead.

Subjects with no lesions, measurable and non-measurable disease were eligible for inclusion in this study. Measurable disease was defined by the presence of ≥1 measurable lesion (longest diameter [LD]≥10 mm with spiral computed tomography [CT] scan or ≥20 mm with conventional CT, magnetic resonance imaging [MRI], or X-Ray). A maximum of 5 measurable lesions (with a maximum of 2 lesions per organ), representative of all lesions involved, were to be identified as target lesions (TL) at baseline. The RECIST 1.1 criteria used to determine objective tumor response for TLs are summarized in Table 3.

TABLE 3

| Overall tumor response for target lesions | |
| --- | --- |
| Complete response (CR) | Disappearance of all TLs since baseline (Any pathological lymph nodes must have reduction in short axis to <10 mm.) |
| Partial response (PR) | >=30% decrease in the sum of the LDs of TLs since baseline |
| Stable disease (SD) | Neither sufficient shrinkage to qualify for PR nor sufficient increase to qualify for PD |
| Progressive disease (PD) | >=20% increase in the sum of the LDs of TLs taking as reference the smallest sum LD recorded since the start of treatment |

All other lesions (or sites of disease) not recorded as TLs were identified as non-target lesions (NTLs). The RECIST criteria used to determine objective tumor response for NTLs are summarized in Table 4.

TABLE 4

| Overall tumor response for non-target lesions. | |
| --- | --- |
| Complete response (CR) | Disappearance of all NTLs since baseline (Any pathological lymph nodes must have reduction in short axis to <10 mm.) |
| Incomplete response (IR)/ Stable disease (SD) | Persistence of >=1 NTLs |
| Progressive disease (PD) | Unequivocal progression could be due to progression in one lesion only, or in several lesions and must be clinically significant, as assessed by the study physician |

Details of any new lesions were also recorded; the presence of ≥1 new lesions was assessed as progression. RECIST evaluation for overall response is summarized in Table 5.

TABLE 5

| Target lesions | Non-target lesions | New lesions | Overall response |
|---|---|---|---|
| A. Time point response: subjects with target (+/−non-target) lesion at baseline ||||
| CR | CR, NA | No | CR |
| CR | SD, NE | No | PR |
| PR | CR, SD, NE, NA | No | PR |
| SD | CR, SD, NE, NA | No | SD |
| NE | CR, SD, NE, NA | No | NE |
| PD | CR, SD, PD, NE, NA | Yes, No | PD |
| CR, PR, SD, NE | PD | Yes, No | PD |
| CR, PR, SD, NE | CR, SD, PD, NE, NA | Yes | PD |
| B. Time point response: subjects with non-target lesion only at baseline ||||
| NA | CR | No | CR |
| NA | SD | No | SD |
| NA | NE | No | NE |
| NA | PD | No | PD |
| NA | CR, SD, NE | Yes | PD |
| C. Time point response: subjects without target and non-target lesion at baseline ||||
| NA | NA | No | NE |
| NA | NA | Yes | PD |
| D. List of Abbreviations ||||
| AE | Adverse Event |||
| CR | Complete Response |||
| CT | Computed Tomography |||
| EVA | Evaluable Population |||
| FAS | Full Analysis Set |||
| IR | Incomplete Response |||
| ITT | Intent-to-treat |||
| LD | Longest Diameters |||
| MRI | Magnetic Resonance Imaging |||
| NA | Not Applicable |||
| NE | Not Evaluable |||
| NEJM | New England Journal of Medicine |||
| NCI | National Cancer Institute |||
| NTL | Non-Target Lesion |||
| PD | Progressive Disease |||
| PFS | Progression Free Survival |||
| PP | Per-protocol |||
| PR | Partial Response |||
| PT | Preferred Term |||
| RECIST | Response Evaluation Criteria In Solid Tumors |||
| SAEs | Serious Adverse Event (s) |||
| SD | Stable Disease |||
| SOC | System Organ Class |||
| TEAE | Treatment Emergent Adverse Event |||
| TL | Target Lesion |||

Study Population:

Disposition of Patients: The following patient data was summarized and presented for all recruited subjects: Number and percentage of patients screened, received study drug, completed and terminated during treatment period, completed and discontinued during follow-up period.

Number and percentage of patients in each analysis set and reason for exclusion, by study group for all recruited patients.

Protocol violations are reviewed by the study team prior to database lock to determine which violations disqualify the patient from the EVA population.

Clinical Result: Negative Control (Patient No: 065) (FIG. 10): The date of assessment was initiated on or before Mar. 18, 2015. It indicated that treating OBI-822 does not lead to any tumor production within 28 weeks (Visit 7). Therefore, the safety of OBI-822 was confirmed.

Figure 11:
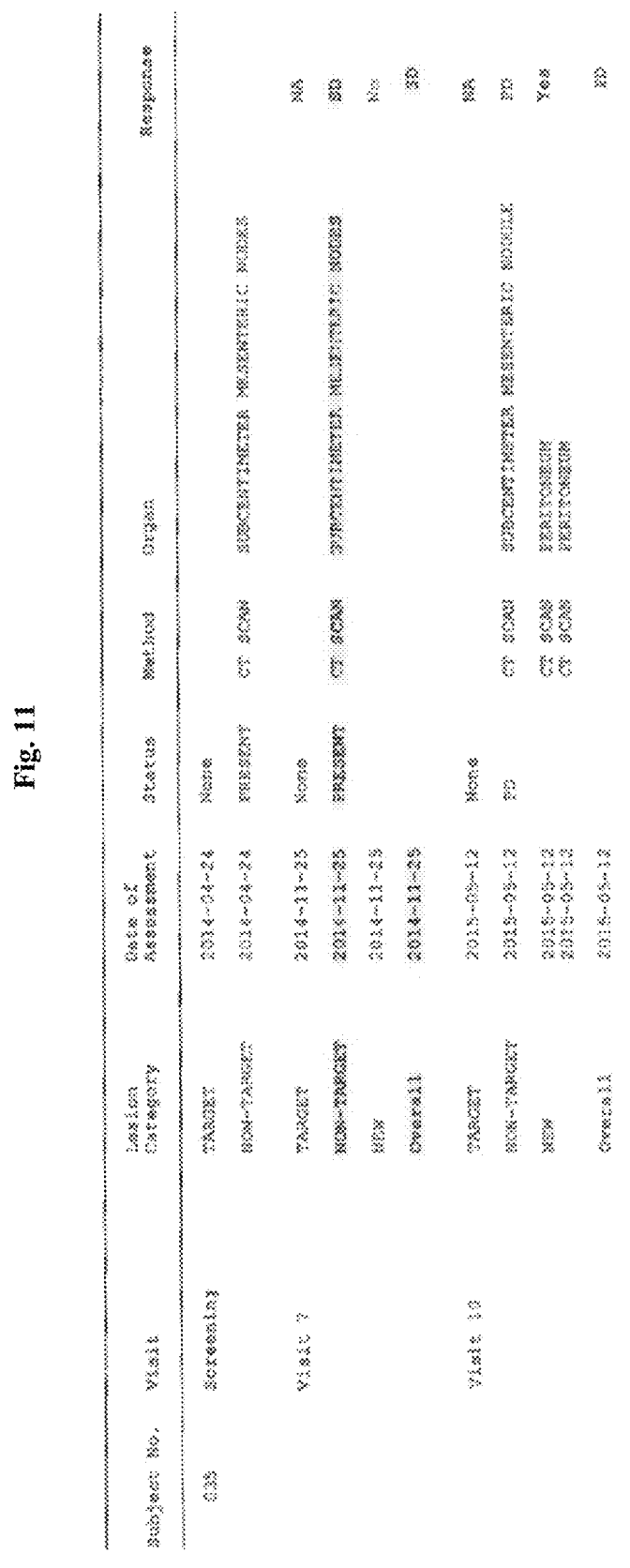

Stage III Ovarian Cancer (Patient No: 035) (FIG. 11): The date of assessment was initiated on or before Apr. 24, 2014. The original symptom of patient was "Sub-centimeter Mesenteric Nodes tumor" (Lesion Category: Non-target tumor) through CT scan. It indicated that there was not any tumor progression/metastasis (SD) after treating OBI-822 within 28 weeks (Visit 7). Therefore, the tumor inhibition ability of OBI-822 is confirmed within 28 weeks.

Figure 12:
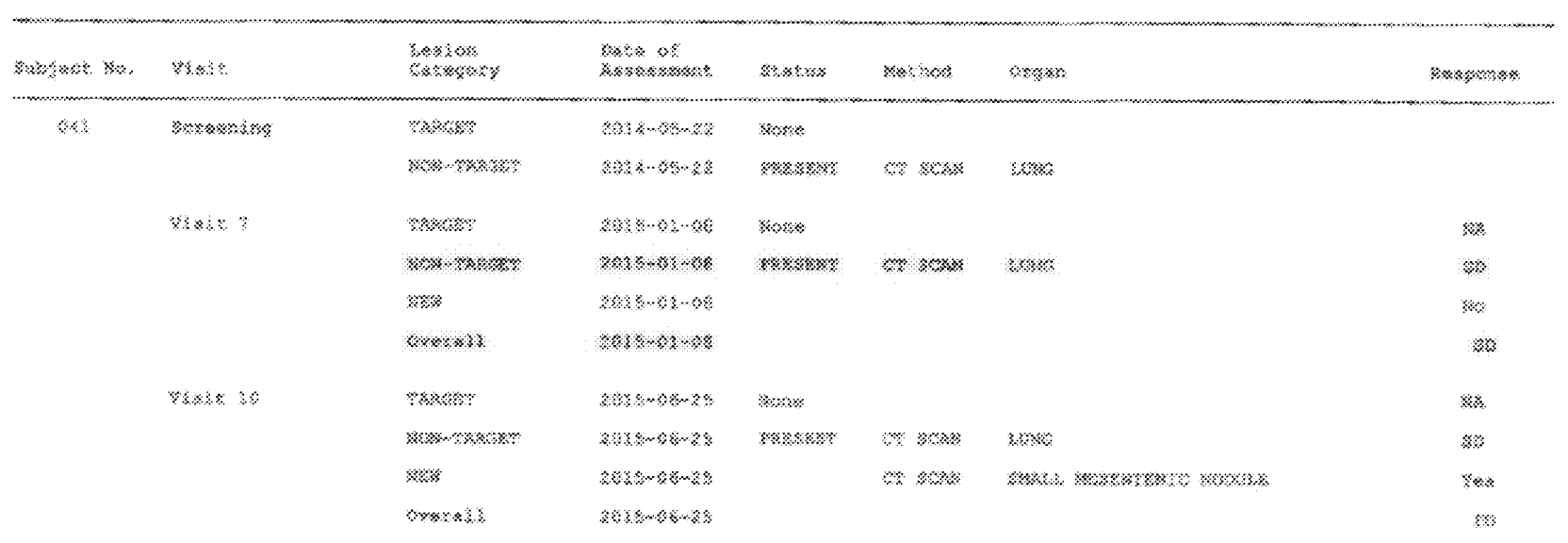

Stage IV Fallopian Tube Cancer (Patient No: 041) (FIG. 12): The date of assessment initiated on or before May 22, 2014. The original symptom of patient was "Lung tumor" (Lesion Category: Non-target tumor) through CT scan. It indicated that there was not any tumor progression/metastasis (SD) after treating OBI-822 within 28 weeks (Visit 7). Therefore, the tumor inhibition ability of OBI-822 is confirmed within 28 weeks.

Stage III Ovarian Cancer (Patient No: 060) (FIG. 13): The date of assessment initiated on or before Jan. 6, 2015. The original symptom of patient was "Peritoneum tumor" (Lesion Category: Non-target tumor) through CT scan. It indicated that there was not any tumor progression/metastasis (SD) after treating OBI-822 within 28 weeks (Visit 7). Therefore, the tumor inhibition ability of OBI-822 is confirmed within 28 weeks.

Example 3

Mixing Instruction for OBI-822 and OBI-821

Storage Condition: OBI-822 and its placebo PBS vials are stored at 2-8° C. OBI-821 and its placebo PBS vials are stored at −15 to −25° C.

Study Groups:

Group A: Active treatment group; Dosage Per Injection: OBI-822 (Equivalent to 30 µg of Globo H)/100 µg of OBI-821. Total final injection volume: 0.8 mL.

Group B: Control group; Dosage Per Injection: PBS. Total final injection volume: 0.8 mL.

Investigational Drugs:

Vial 1a (PBS: OBI-821 control test article) Fill Volume—0.5 mL. Contents: 10 mM sodium phosphate, 150 mM NaCl, pH 6.8;

Vial 1b (OBI-821) Fill Volume—0.5 mL. Contents: 250 µg/mL OBI-821 in 10 mM sodium phosphate, 150 mM NaCl, pH 6.8;

Vial 2a (PBS: OBI-822 control test article) Fill Volume—0.75 mL. Contents: 100 mM sodium phosphate, 150 mM NaCl, pH 7.2;

Vial 2b (OBI-822) Fill Volume—0.75 mL. Contents: Equivalent to 75 µg of Globo H/mL OBI-822 in 100 mM sodium phosphate, 150 mM NaCl, pH 7.2.

Mixing Instruction for OBI-822 and OBI-821:

At time of treatment, with syringe, withdraw 0.5 mL of Vial 2a (PBS only) and place in Vial 1a (PBS only) or withdraw 0.5 mL of Vial 2b (OBI-822 in PBS) and place in Vial 1b (OBI-821 in PBS). Gently mix the contents of the Vial (either Vial 1a or Vial 1b) by gently inverting the vial 4-5 times. Do not shake the vial vigorously. At this time, this vial contains either Placebo (PBS only) or Treatment (OBI-822 plus OBI-821) and is ready for injection. Then withdraw 0.8 mL of from this vial for subject injection. The final administration volume of each study group is summarized in Table 6.

TABLE 6

The calculation of final administration volume of study groups

| Group | Volume (mL) Added/Used | | | | Total Volume after Reconstitution (mL) | Total Administered Volume per Dose (mL) |
|---|---|---|---|---|---|---|
| | Vial 1a PBS (OBI-821 Control Test) | Vial 1b OBI-821 | Vial 2a PBS (OBI-822 Control Test) | Vial 2b OBI-822 | | |
| A | 0 | 0.5 | 0 | 0.5 | 1.0 | 0.8 |
| B | 0.5 | 0 | 0.5 | 0 | 1.0 | 0.8 |

The stability of the combined OBI-822 and OBI-821 is stable up to 10 hours from the time of reconstitution at room temperature. The administration of the combined product should occur within 2 hours from reconstitution to minimize potential microbial growth. If administration is not possible within 2 hours from reconstitution, the combined product should be destroyed according to the institutional pharmacy Standard Operating Procedure and documented in the drug accountability records. FIG. 14 illustrates the mixing procedure of investigational drugs Example 4

Permitted and Prohibited Concomitant Medication

Permitted Concomitant Medications:

Opiates: It may be used for pain control, and preventive treatment for constipation is also allowed.

GCSF: Will be allowed if deemed necessary by doctors.

Bisphosphonate.

Hormone therapies (for subjects who have been stratified as a hormone therapy user).

If used, the selected form, dose, or usage of hormone therapy needs to be consistent i.e., no switching of treatments, no adding of more therapies, or increasing doses, unless due to intolerance of toxicity. All kind of hormone therapies can be used in this study, the common used hormone therapies are listed below.

Estrogen inhibitors (e.g., tamoxifen, Fareston).

Aromatase inhibitors (e.g., anastrozole [Arimidex], exemestane [Aromasin] and letrozole [Femara]).

Pituitary downregulators (e.g., goserelin [Zoladex], leuprolide [Lupron])—These are also called LHRH analogues.

Novaldex® (tamoxifen selective estrogen-receptor modulator, SERM).

Evista® (rolaxifene, another SERM).

Faslodex® (fulvestran, estrogen receptor down-regulator).

Anticoagulant (lepirudin [Refludan]).

Enzyme (rasburicase [Elitek]).

Hematopoietic growth factors.

The method of administrations is preferably conducted in the absence of the concomitant medications listed in Table 7.

TABLE 7

| Concomitant Medications | | |
|---|---|---|
| Anti-neoplastic Agents: | | Radiotherapy |
| Antimetabolites | Miscellaneous | Surgery for the metastatic breast cancer |
| Vinca alkaloid | cytotoxic agents | |
| Epipodophyllotoxins | Alkylating agents | |
| Taxanes | Antitumor antibiotics | |
| Camptothecins | Nitrosoureas | |
| Biologic Agents: | | Glucocorticoid steroids |
| HER1/EGFR tyrosine kinase inhibitor: (erlotinib [Tarceva]) | | Should not be used, however, topical or temporary systemic steroid use may be |
| VEGF protein inhibitor: bevacizumab (Avastin) | | allowed, if clinically indicated. In the event |
| HER-2/ErbB2 inhibitors: lapatinib (Tyverb/Tykerb) | | of mild to moderate autoimmune disorders, |
| Interferons | | temporary use of systemic steroids is |
| Interleukins | | allowed. |
| Monoclonal antibodies | | Hormone therapies (for subjects who have been stratified as a hormone therapy non-user) |
| Immunosuppressive therapy | | |

Prohibited Concomitant Medications (e.g., cyclosporin, rapamycin, tacrolimus, rituximab, etc.).

Eastern Cooperative Oncology Group (ECOG) Performance.

These scales and criteria are used by doctors and researchers to assess how a subject's disease is progressing, assess how the disease affects the daily living abilities of the subject, and determine appropriate treatment and prognosis. They are included in table 8 for health care professionals to access.

TABLE 8

Eastern Cooperative Oncology Group (ECOG) Performance
ECOG Performance Status

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of only limited self-care, confined to bed or chair more than 50% of waking hours |
| 4 | Completely disabled. Cannot carry on any self-care. Totally confined to bed or chair |
| 5 | Dead |

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference in its entirety for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method for treating a breast cancer or an ovarian cancer comprising administering to a human subject in need thereof a therapeutically effective dose of a Globo H-KLH (Keyhole limpet hemocyanin) glycoconjugate vaccine nine or more times;
   wherein the Globo H-KLH glycoconjugate vaccine is OBI-822; and
   wherein the therapeutically effective dose is 30 µg.

2. The method of claim 1, wherein the Globo H-KLH glycoconjugate vaccine is administered as a pharmaceutical composition.

3. The method of claim 2, wherein the pharmaceutical composition further comprises an adjuvant.

4. The method of claim 3, wherein the adjuvant is selected from saponin, Freund's adjuvant or α-galactosyl-ceramide (α-GalCer) adjuvant.

5. The method of claim 2, wherein the pharmaceutical composition comprises OBI-822 vaccine and OBI-821 adjuvant.

6. The method of claim 1, whereby the administration results in an immune response induced by the Globo H-KLH glycoconjugate vaccine.

7. The method of claim 1, wherein the administration procedure comprises intramuscular injection, subcutaneous injection, intravenous injection, intraperitoneal injection, intra-arterial injection, intrasynovial injection, intrathecal injection, epidural injection or intra-pleural injection.

8. The method of claim 1, wherein the vaccine is administered intermittently at a time interval of one week to five years or more.

9. The method of claim 1, wherein the vaccine is administered once every one week, once every two weeks, once every three weeks, once every four weeks, once every five weeks, once every six weeks, once every seven weeks, once every eight weeks, once every nine weeks, once every ten weeks, once every eleven weeks or once every twelve weeks.

10. A method for treating a breast cancer or an ovarian cancer comprising administering to a human subject in need thereof a pharmaceutically effective amount of Globo H-KLH (Keyhole limpet hemocyanin) glycoconjugate vaccine;
    wherein the pharmaceutically effective amount of the Globo H-KLH glycoconjugate vaccine is 30 µg;
    wherein the administration is nine or more times and
    wherein the Globo H-KLH glycoconjugate vaccine is OBI-822.

11. The method of claim 10, wherein the vaccine further comprises an adjuvant.

12. The method of claim 11, wherein the adjuvant is selected from saponin, Freund's adjuvant or α-galactosyl-ceramide (α-GalCer) adjuvant.

13. The method of claim 12, wherein the saponin adjuvant is OBI-821.

14. The method of claim 10, wherein the Globo H-KLH glycoconjugate vaccine comprises OBI-822 and a pharmaceutically acceptable excipient.

15. The method of claim 10, whereby the administration results in an immune response induced by the Globo H-KLH glycoconjugate vaccine.

16. The method of claim 10, whereby the administration of the Globo H-KLH glycoconjugate vaccine induces an immunogenic production of monoclonal antibody directed to Globo H.

17. The method of claim 16, wherein the antibody produced is an IgG, an IgM, or both.

18. The method of claim 10, wherein the tumor is metastatic or non-metastatic.

19. The method of claim 10, wherein the Globo H-KLH glycoconjugate vaccine is administered to the patient in combination with one or more anti-proliferative agents.

20. The method of claim 19, wherein the anti-proliferative agent is selected from cyclophosphamide, opiate, granulocyte colony-stimulating factor (GCSF), estrogen inhibitors, aromatase inhibitors, pituitary downregulators, tamoxifen selective estrogen-receptor modulator, raloxifine, estrogen receptor down-regulator, anticoagulant, enzyme, hematopoietic growth factor, anti-neoplastic agent, antimetabolites, miscellaneous cytotoxic agents, vinca alkaloid, epipodophyllotoxins, alkylating agents, taxanes, antitumor antibiotics, camptothecins, nitrosoureas, HER1/EGFR tyrosine kinase inhibitor, VEGF protein inhibitor, HER-2/ErbB2 inhibitor, interferon, interleukin, monoclonal antibody, or glucocorticoid steroid.

21. The method of claim 19, wherein the anti-proliferative agent is selected from erlotinib, docetaxel, gemcitabine, cisplatin; carboplatin; paclitaxel, trastuzumab, temozolomide, tamoxifen, doxorubicin, oxaliplatin, bortezomib, sutent, letrozole, imatinib mesylate, MEK inhibitor, fulvestrant, leucovorin (folinic acid); rapamycin, lapatinib, lonafarnib, sorafenib, gefitinib, irinotecan, tipifarnib, Cremophor-free, paclitaxel, vandetanib, chloranmbucil, temsirolimus, pazopanib, canfosfamide, thiotepa, cyclosphosphamide, 5-fluorouracil (5-FU), vinorelbine, novantrone, teniposide, edatrexate, daunomycin, aminopterin, capecitabine, ibandronate, topoisomerase inhibitor RFS 2000, difluoromethylornithine (DMFO), tamoxifen, raloxifene, droloxifene, 4-hydroxytamoxifen, trioxifene, keoxifene, onapristone, toremifine citrate, 4(5)-imidazoles, aminoglutethimide, megestrol acetate, exemestane, formestanie, fadrozole, vorozole, letrozole, anastrozole, flutamide, nilutamide, bicalutamide, leuprolide, goserelin, troxacitabine (α-1,3-dioxolane nucleoside cytosine analog), lipid kinase inhibitor, oblimersen, angiozyme, allovectin, leuvectin, vaxid, aldesleukin, lurtotecan, abarelix, bevacizumab, alemtuzumab, cetuximab, panitumumab, rituximab, pertuzumab, trastuzumab, tositumomab, gemtuzumab or ozogamicin.

22. A method for improving overall survival (OS) or progression free survival (PFS) of a human subject afflicted with a breast cancer or an ovarian cancer comprising administering to the human subject in need thereof;
  a therapeutically effective dose of Globo H-KLH (Keyhole limpet hemocyanin) glycoconjugate vaccine nine or more times;
  wherein the therapeutically effective amount of the Globo H-KLH glycoconjugate vaccine is 30 µg; and
  wherein the Globo H-KLH glycoconjugate vaccine is OBI-822.

23. The method of claim 22, whereby the administration results in an immune response induced by the Globo H-KLH glycoconjugate vaccine.

24. The method of claim 23, wherein the immune response is selected from IgG, IgM or cell-mediated response.

25. The method of claim 24, wherein the cell is B cell or T cell.

26. The method of claim 22, wherein the Globo H-KLH glycoconjugate vaccine further performs one or more of the following actions:
  (a) induces Antibody-Dependent Cellular Cytotoxicity (ADCC) and Complement-Dependent Cytotoxicity (CDC) to kill solid tumors;
  (b) induces an anti-Globo series antigens-specific IgM/IgG immune response;
  (c) traps Globo series antigens-ceramide shedding from tumor cells thereby blocking translin-associated factor X (TRAX)-dependent angiogenesis;
  (d) induces anti-Globo series antigens antibodies to block Globo series antigens-ceramide induced Notch 1-dependent immunosuppression thereby enhancing T cell proliferation and cytokine production;
  (e) induces apoptosis of tumor cells; or
  inhibits Globo series antigens induced angiogenesis;
  and wherein the Globo series antigens is Globo H, Stage-specific embryonic antigen 3 (SSEA-3) or Stage-specific embryonic antigen 4 (SSEA-4).

27. The method of claim 22, wherein the human subject administered with the therapeutically effective dose of the Globo H-KLH glycoconjugate vaccine or the pharmaceutically effective amount of the Globo H-KLH glycoconjugate vaccine has the overall survival (OS) at least 10% higher than a control group at 20 months since date of randomization or at least 30% higher than the control group at 32 months since date of randomization.

28. A method for inducing/enhancing an immune response in a human subject having a breast cancer or an ovarian cancer, comprising administering to the subject;
  a therapeutically effective dose of Globo H-KLH (Keyhole limpet hemocyanin) glycoconjugate vaccine nine times;
  wherein the therapeutically effective amount of the Globo H-KLH glycoconjugate vaccine is 30 µg;
  wherein the Globo H-KLH glycoconjugate vaccine is OBI-822; and
  wherein the immune response is selected from IgG, IgM or cell-mediated response.

29. The method of any of claim 1, 10, 22, or 28, wherein the vaccine further comprises immune response booster agents.

30. The method of any of claim 1, 10, 22, or 28, wherein the administration is nine times.

31. The method of any of claim 1, 10, 22, or 28, wherein the breast cancer is stage I, II, III, ER(+), PR(+), HER2(+), triple negative, metastatic or non-metastatic.

* * * * *